(12) United States Patent
Murphy et al.

(10) Patent No.: US 9,889,144 B2
(45) Date of Patent: Feb. 13, 2018

(54) ABIRATERONE ACETATE FORMULATION AND METHODS OF USE

(71) Applicant: iCeutica Inc., Philadelphia, PA (US)

(72) Inventors: Maura Murphy, Philadelphia, PA (US); Paul Nemeth, Philadelphia, PA (US); H. William Bosch, Philadelphia, PA (US); Matthew Callahan, Philadelphia, PA (US); Satya Bhamidipati, Philadelphia, PA (US); Jason Coleman, Philadelphia, PA (US); Christopher Hill, Philadelphia, PA (US); Marck Norret, Darlington (AU)

(73) Assignee: iCeutica Inc., Philadelphia, PA (US)

( * ) Notice: Subject to any disclaimer, the term of this patent is extended or adjusted under 35 U.S.C. 154(b) by 0 days.

(21) Appl. No.: 15/645,895

(22) Filed: Jul. 10, 2017

(65) Prior Publication Data

US 2017/0348328 A1 Dec. 7, 2017

Related U.S. Application Data

(63) Continuation of application No. 14/707,922, filed on May 8, 2015, which is a continuation-in-part of application No. PCT/US2014/030642, filed on Mar. 17, 2014, and a continuation-in-part of application
(Continued)

(51) Int. Cl.
*A61K 31/56* (2006.01)
*A61K 31/58* (2006.01)
*A61K 9/20* (2006.01)
*A61K 31/19* (2006.01)
(Continued)

(52) U.S. Cl.
CPC ............ *A61K 31/58* (2013.01); *A61K 9/2054* (2013.01); *A61K 31/19* (2013.01); *A61K 31/573* (2013.01); *A61K 9/145* (2013.01); *Y10T 428/2982* (2015.01)

(58) Field of Classification Search
USPC ........................................ 514/170, 171, 182
See application file for complete search history.

(56) References Cited

U.S. PATENT DOCUMENTS

| | | |
|---|---|---|
| 5,478,705 A | 12/1995 | Czekai et al. |
| 5,500,331 A | 3/1996 | Czekai et al. |
| 5,604,213 A | 2/1997 | Barrie et al. |

(Continued)

FOREIGN PATENT DOCUMENTS

| | | |
|---|---|---|
| CN | 102743393 | 10/2012 |
| WO | WO 2008/000042 | 1/2008 |

(Continued)

OTHER PUBLICATIONS

Clinicaltrials.gov. A Comparative Study of Bioavailability of 3 New Abiraterone Acetate Tablets With Current Commercial Tablet. NCT01640093. pp. 1-3 [online]. 2013 (retrieved on Nov. 3, 2015] Retrieved from the internet; URL: <https://clinicaltrials.gov/ct2/show/NCT01640093?term=zytiga&rank=3>; p. 1, official title; p. 2, table.

(Continued)

*Primary Examiner* — San-Ming Hui
(74) *Attorney, Agent, or Firm* — Fish & Richardson P.C.; Vasily A. Ignatenko

(57) ABSTRACT

Pharmaceutical compositions, including unit dosage forms, comprising abiraterone acetate and methods for producing and using such compositions are described.

20 Claims, 2 Drawing Sheets

Related U.S. Application Data

No. 14/282,535, filed on May 20, 2014, now abandoned.

(60) Provisional application No. 61/789,141, filed on Mar. 15, 2013, provisional application No. 61/883,941, filed on Sep. 27, 2013, provisional application No. 62/052,294, filed on Sep. 18, 2014.

(51) Int. Cl.
*A61K 31/573* (2006.01)
*A61K 9/14* (2006.01)

(56) References Cited

U.S. PATENT DOCUMENTS

| | | |
|---|---|---|
| 6,514,524 B1 | 2/2003 | Saslawski |
| 8,470,330 B2 | 6/2013 | Maddon |
| 8,735,450 B2 | 5/2014 | Dodd et al. |
| 8,808,751 B2 | 8/2014 | Cammarano et al. |
| 8,822,438 B2 | 9/2014 | Auerbach et al. |
| 9,095,496 B2 | 8/2015 | Dodd et al. |
| 2007/0281934 A1 | 12/2007 | Buggy |
| 2008/0004257 A1 | 1/2008 | Chan et al. |
| 2008/0051380 A1 | 2/2008 | Auerbach et al. |
| 2009/0088424 A1 | 4/2009 | Zalit et al. |
| 2009/0124587 A1 | 5/2009 | Auerbach et al. |
| 2012/0160944 A1 | 6/2012 | Dodd |
| 2013/0122085 A1 | 5/2013 | Dalton et al. |
| 2014/0287039 A1 | 9/2014 | Bosch et al. |
| 2015/0157646 A1 | 6/2015 | Nemeth et al. |
| 2015/0246060 A1 | 9/2015 | Murphy et al. |
| 2017/0049788 A1 | 2/2017 | Nemeth et al. |

FOREIGN PATENT DOCUMENTS

| | | |
|---|---|---|
| WO | WO 2008/024484 | 2/2008 |
| WO | WO 2010/121322 | 10/2010 |
| WO | WO 2010/121323 | 10/2010 |
| WO | WO 2012/140220 | 10/2012 |
| WO | WO 2013/164473 | 11/2013 |
| WO | WO 2014/009434 | 1/2014 |
| WO | WO 2014/009436 | 1/2014 |
| WO | WO 2014/009437 | 1/2014 |
| WO | WO 2014/083512 | 6/2014 |
| WO | WO 2014/145813 | 9/2014 |

OTHER PUBLICATIONS

International Preliminary Report on Patentability in corresponding PCT Application No. PCT/US14/30642, dated Sep. 15, 2015, pp. 1-12.

International Preliminary Report on Patentability in corresponding International Application No. PCT/US2015/050889, dated Mar. 21, 2017, 16 pages.

International Search Report and Written Opinion in corresponding PCT Application No. PCT/US14/30642, dated Aug. 12, 2014, pp. 1-13.

International Search Report and Written Opinion in corresponding PCT Application No. PCT/US155/50889, dated Dec. 17, 2015, 19 pages.

Janssen-Cilag International N.V., "Assessment Report for Zytiga (abiraterone) Procedure No. EMEA/H/C/002321" 2011 http://www.ema.europa.eu/docs/en_GB/document_library/EPAR_-_Public_assesment_report/human/002321/WC500112860.pdf, pp. 1-13.

Remington Pharmaceutical Science. 17th ed., 1985, pp. 1278-1282 and 1409-1419.

Zytiga® (abiraterone acetate) Tablets, Patient Information, Janssen Biotech, Inc., © 2012, revised May 2015, 9 pages.

ABIRATERONE ACETATE FORMULATION AND METHODS OF USE

RELATED APPLICATIONS

This application is a continuation and claims priority to application Ser. No. 14/707,922, filed on May 8, 2015, which is a continuation-in-part and claims priority to Application No. PCT/US2014/030642, filed on Mar. 17, 2014, which claims priority under 35 USC §119(e) to provisional U.S. Patent Application No. 61/789,141, filed on Mar. 15, 2013, and provisional U.S. Patent Application No. 61/883,941, filed on Sep. 27, 2013; and which application Ser. No. 14/707,922 is also a continuation-in-part and claims priority to application Ser. No. 14/282,535, filed on May 20, 2014, which claims priority under 35 USC §119(e) to provisional U.S. Patent Application No. 61/883,941, filed on Sep. 27, 2013; and which application Ser. No. 14/707,922 also claims priority under 35 USC §119(e) to provisional U.S. Patent Application No. 62/052,294, filed on Sep. 18, 2014. The entire contents of the foregoing are hereby incorporated by reference in their entirety.

FIELD OF THE DISCLOSURE

The present disclosure relates to methods for producing particles of abiraterone acetate as well as compositions containing abiraterone acetate and methods of treatment using compositions containing abiraterone acetate.

BACKGROUND

Abiraterone ((3β)-17-(pyridin-3-yl) androsta-5, 16-dien-3-ol; CAS #: 154229-19-3; Formula: $C_{24}H_{31}NO$; Mol. Weight: 349.5 g/mol) is an inhibitor of CYP17 and thus interferes with the synthesis of androgens in the testes, adrenal glands and prostate tumor tissue. Abiraterone acetate (17-(3-Pyridyl) androsta-5, acetate; CAS #154229-18-2), a prodrug of abiraterone, is approved in the United States for treatment of castration-resistant prostate cancer. Abiraterone acetate is considered poorly water soluble.

Zytiga® Tablets (250 mg; National Drug Code Number 57894-150; NDA 202379) are approved in the United States in combination with prednisone for the treatment of patients with metastatic castration-resistant prostate cancer. The prescribing information for Zytiga® tablets recommends 1,000 mg (4×250 mg tablets) administered orally once daily in combination with prednisone (5 mg) administered orally twice daily. The European approval of Zytiga® is for administration in combination with either prednisone or prednisolone.

Prescribing information for Zytiga® states that it must be taken on an empty stomach and that no food should be consumed for at least two hours before the dose is taken and for and for at least one hour after the dose is taken. The prescribing information explains that at a dose of 1,000 mg daily in patients with metastatic, castration resistant prostate cancer the steady-state values (mean±SD) of Cmax were 226±178 ng/mL and of AUC were 1173±690 ng·hr/mL. A single dose (1000 mg) cross-over study of Zytiga® in healthy subjects found that systemic exposure of abiraterone is increased when Zytgia® is administered with food. Specifically, abiraterone $C_{max}$ and $AUC_{0-\infty}$ were approximately 7- and 5-fold higher, respectively, when Zytiga® was administered with a low-fat meal (7% fat, 300 calories) compared to administration in the fasted state. Abiraterone $C_{max}$ and $AUC_{0-\infty}$ were approximately 17- and 10-fold higher, respectively, when Zytiga® was administered with a high-fat (57% fat, 825 calories) meal compared to administration in the fasted state.

SUMMARY

The present disclosure features pharmaceutical compositions, including unit dosage forms, comprising abiraterone acetate as well as methods for producing and using such compositions.

Described herein is unit dosage form of abiraterone acetate, wherein a 500 mg dose of the unit dosage form is bioequivalent to a 1000 mg dose of Zytiga® in healthy male subjects in the fasted state. Also described is: a unit dosage form of abiraterone acetate, wherein the ratio of the log of the geometric mean of the $AUC_{(0-\infty)}$ for a 500 mg dose administered to healthy male subjects in the fasted state compared to a 1000 mg dose of Zytiga® administered to healthy male subjects in the fasted state is selected from: 0.6 to 1.4, 0.7 to 1.3, 0.8 to 1.2 and 0.9 to 1.1; a unit dosage form of abiraterone acetate, wherein the ratio of the log of the geometric mean of the C(max) for a 500 mg dose administered to healthy male subjects in the fasted state compared to a 1000 mg dose of Zytiga® administered to healthy male subjects in the fasted state is selected from: 0.6 to 1.4, 0.7 to 1.3, 0.8 to 1.2 and 0.9 to 1.1.

In some cases: the [D90] of the abiraterone acetate is greater than 300 nm and less than one of: 7500 nm, 7000 nm, 6000 nm, 5000 nm, 4500 nm, 4000 nm, 3000 nm, 2000 nm, 900 nm, 800 nm, and 700 nm; the [D50] of the abiraterone acetate greater than 100 nm and is less than one of: 3500 nm, 3000 nm, 2500 nm, 1600 nm, 1400 nm, 1200 nm, 1000 nm, 800 nm, 500 nm, 400 nm, and 300 nm; the [D4,3] of the abiraterone acetate is greater than 300 nm and less than one of: 7000 nm, 6000 nm, 5000 nm, 4000 nm, 3000 nm, 2500 nm, 2400 nm, 2200 nm, 2000 nm, 1900 nm, 1700 nm, 1500 nm, 1300 nm, 1100 nm, 900 nm, and 800 nm; the dissolution rate of the abiraterone acetate in the unit dosage form is such that when a sample containing 100 mg of abiraterone acetate is tested in 900 ml of pH 4.5 phosphate buffer with 0.1% sodium lauryl sulfate using USP Apparatus II at 75 rpm, at least 70% of the abiraterone acetate dissolves in between 5 and 15 min or between 5 and 10 min; the dissolution rate of the abiraterone acetate in the unit dosage form is such that when a sample containing 125 mg of fine particle abiraterone acetate is tested in 900 ml of pH 4.5 phosphate buffer with 0.12% sodium lauryl sulfate using USP Apparatus II at 75 rpm, at least 70% of the abiraterone acetate dissolves in between 5 and 15 min or between 5 and 10 min; the unit dosage form contains 125 mg of abiraterone acetate.

Also described is a unit dosage form of a pharmaceutical composition comprising abiraterone acetate, wherein a 500 mg dose, upon oral administration to a population of healthy male subjects in the fasted state, provides a mean blood plasma Cmax of 50-120 ng/ml. In some cases: a 500 mg dose, upon oral administration to a population of healthy male subjects in the fasted state, provides a median blood plasma tmax of 1 to 2.5 hrs. Described herein is a unit dosage form of a pharmaceutical composition comprising abiraterone acetate, wherein a 500 mg dose, upon oral administration to a population of healthy male subjects in the fasted state, provides a mean blood plasma AUC (0-∞) of 240-650 h*ng/ml. In some case the unit dosage form contains 125 mg of abiraterone acetate.

Also described is: a unit dosage form of a pharmaceutical composition comprising of abiraterone acetate, wherein the 90% confidence interval of the mean blood plasma Cmax is a value between 50 and 120 ng/ml when a 500 mg dose is administered to healthy male subjects in the fasted state; and a unit dosage form of a pharmaceutical composition comprising of abiraterone acetate, wherein the 90% confidence interval of the mean blood plasma AUC (0-∞) is a value between 240 and 650 h*ng/ml when a 500 mg dose is administered to healthy male subjects in the fasted state.

The unit dosage forms described herein can contain an antioxidant (e.g., one or both of BHA and BHT).

Also described herein is a method for treating castration resistant prostate cancer comprising administering to a patient in need thereof a therapeutically effective dose (e.g., 500 mg) of the unit dosage form of abiraterone acetate described herein and a glucocorticoid. In various embodiments: the glucocorticoid is selected from the group consisting of prednisone, prednisolone and methylprednisolone; the therapeutically effective dose is 500 mg/day; the therapeutically effective dose is administered using dosage forms containing: 100 mg, 125 mg, or 150 mg of abiraterone acetate; the 500 mg dose is administered using 1, 2, 3, 4, 5, or 6 unit dosage forms.

Described herein is a method for producing a composition comprising abiraterone acetate, the method comprising: dry milling a composition comprising abiraterone acetate, a millable grinding compound, a facilitating agent and one or both of an antioxidant and a sequestering agent in a mill, for a time period sufficient to produce a composition comprising milled abiraterone acetate, wherein the particle size of the abiraterone acetate is reduced by dry milling.

In some cases of the method for production: the [D90] of the abiraterone acetate in the milled composition is greater than 400 nm and less than one of: 7500, 7000, 6000 nm, 5000 nm, 4500 nm, 4000 nm, 3000 nm, 2000 nm, 900 nm, 800 nm, and 700 nm; the [D50] of the abiraterone acetate in the milled composition is greater than 100 nm and is less than 3500 nm, 3000 nm, 2500 nm, less than 1600 nm, less than 1400 nm, less than 1200 nm, less than 1000 nm, less than 800 nm, less than 500 nm, less than 400 nm, less than 300 nm; the dissolution rate of the abiraterone acetate in the milled composition is such that when a sample containing 100 mg of abiraterone acetate is tested in 900 ml of pH 4.5 phosphate buffer with 0.1% sodium lauryl sulfate using USP Apparatus II at 75 rpm, at least 70% of the abiraterone acetate dissolves in between 5 and 15 min or between 5 and 10 min; the dissolution rate of the abiraterone acetate in the milled composition is such that when a sample containing 125 mg of abiraterone acetate is tested in 900 ml of pH 4.5 phosphate buffer with 0.12% sodium lauryl sulfate using USP Apparatus II at 75 rpm, at least 70% of the abiraterone acetate dissolves in between 5 and 15 min or between 5 and 10 min; the [D50] of the abiraterone acetate in the milled composition is greater than 200 nm and is less than 6500 nm, 6000 nm, 5500 nm, less than 5000 nm, less than 4000 nm, less than 3000 nm, or less than 2000 nm; and method the method further comprises: combining the composition comprising fine particles of abiraterone acetate with one or more pharmaceutically acceptable diluents, disintegrants, lubricants, glidants or dispersants to prepare unit dosage form.

In various embodiments, the particles of abiraterone acetate in the pharmaceutical compositions (or used to prepared the pharmaceutical composition) have a median particle size, determined on a particle volume basis ($[D_{50}]$ or $D_{[50]}$ or [D50]), equal or less than a size selected from the group consisting of: 5000 nm, 4000 nm, 3000 nm, 2500 nm, 2400 nm, 2300 nm, 2200 nm, 2200 nm, 2100 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm and 200 nm. In some embodiments, the [D50] is equal to or greater than 25 nm or 100 nm or even 500 nm. In various embodiments the [D50] is between: 5000 nm and 100 nm, 3500 nm and 100 nm, 2500 nm and 100 nm, 1500 nm and 100 nm, 1200 nm and 100 nm, 1100 nm and 100 nm, 1000 nm and 100 nm, 800 nm and 100 nm, 700 nm and 100 nm, 600 nm and 100 nm, 500 nm and 100 nm. The D[4,3] (volume mean diameter) in various embodiments is: less than 7000 nm, less than 5000 nm, less than 3500 nm, less than 3000 nm, less than 2000 nm, less than 1000 or less than 300 nm. In various cases, such as those described previously, the D[4,3] is greater than 100 nm or greater than 200 nm. In some cases the D[4,3] (volume mean diameter) is between: 7000 nm and 1000 nm, 6000 nm and 200 nm, 5000 nm and 1000 nm, 4000 nm and 1000 nm, 3000 nm and 1000 nm, 2000 nm and 1000 nm, 1800 nm and 1000 nm, 1600 nm and 1000 nm, 1500 nm and 1000 nm, 1500 nm and 500 nm, 4000 nm and 2000 nm, 4000 nm and 100 nm, 25000 nm and 500 nm, 700 nm and 100 nm, 600 nm and 100 nm, 500 nm and 100 nm 1000 nm and 200 nm, 900 nm and 200 nm, 800 nm and 200 nm, 700 nm and 200 nm. The [D90] ($[D_{90}]$ or $D_{[90]}$) in various embodiments is: less than 8000 nm, less than 7500 nm, less than 7000 nm, less than 6000 nm, less than 4000 nm, less than 2000 nm, less than 1000 nm, less than 500 nm. In some cases, the D90 is between: 5500 nm and 300 nm, 5000 nm and 500 nm, 4500 nm and 500 nm, 4000 nm and 200 nm, 4500 nm and 750 nm, and 3500 nm and 500 nm. In various embodiments described herein the [D90] of the abiraterone acetate is less than 5000 nm or less than 4000 nm. In some embodiments the $[D_{90}]$ is: 6000 nm-500 nm, 5500 nm-500 nm, or 5000 nm-500 nm, and 4000-400 nm.

In another embodiment, the crystallinity profile of the abiraterone acetate is selected from the group consisting of: at least 20% of the abiraterone acetate is crystalline, at least 30% of the abiraterone acetate is crystalline, at least 40% of the abiraterone acetate is crystalline, at least 50% of the abiraterone acetate is crystalline, at least 60% of the abiraterone acetate is crystalline, at least 70% of the abiraterone acetate is crystalline, at least 75% of the abiraterone acetate is crystalline, at least 85% of the abiraterone acetate is crystalline, at least 90% of the abiraterone acetate is crystalline, at least 95% of the abiraterone acetate is crystalline and at least 98% of the abiraterone acetate is crystalline. In some embodiments, the crystallinity profile of the abiraterone acetate is substantially equal to the crystallinity profile of the abiraterone acetate before the material was subjected to the method as described herein.

In another embodiment, the amorphous content of the abiraterone acetate is selected from the group consisting of: less than 80% of the abiraterone acetate is amorphous, less than 70% of the abiraterone acetate is amorphous, less than 60% of the abiraterone acetate is amorphous, less than 50% of the abiraterone acetate is amorphous, less than 40% of the abiraterone acetate is amorphous, less than 30% of the abiraterone acetate is amorphous, less than 25% of the abiraterone acetate is amorphous, less than 15% of the abiraterone acetate is amorphous, less than 10% of the abiraterone acetate is amorphous, less than 5% of the abiraterone acetate is amorphous and less than 2% of the abiraterone acetate is amorphous. In some embodiments, the abiraterone acetate has no significant increase in amorphous content after subjecting the material to the dry milling method described herein.

In some embodiments, the particles of abiraterone acetate are prepared by dry milling abiraterone acetate with a millable grinding compound and a facilitating agent in the presence of milling bodies. Additional components can be present during the milling and together the various components present during milling (with the exception of abiraterone acetate and the milling bodies) are referred to as a grinding matrix. In some cases, the milling produces particles of abiraterone acetate that are significantly reduced in size dispersed in grinding matrix. Because all of the components in the grinding matrix are pharmaceutically acceptable, pharmaceutical compositions can be prepared using the mixture of abiraterone acetate and grinding matrix produced by the milling. In some cases some or all of the components of the grinding matrix are reduced in size during milling. In some cases additional pharmaceutically acceptable components can be added to the mixture of abiraterone acetate and grinding matrix subsequent to milling. In some embodiments, the dry milling takes place in the presence of milling bodies; in other cases the particles are produced by milling in the absence of milling bodies, for example, by milling in jet mill or another type of mill, for example a mill that can reduce the particle size and/or increase the solubility of abiraterone acetate when the abiraterone acetate is milling in presence of millable grinding compound, which itself may or may not be reduced in particle size.

In some cases abiraterone acetate is milled with one or more millable grinding compounds selected from: lactose (e.g., lactose monohydrate or lactose anhydrous) and mannitol and one or more facilitating agents selected from sodium lauryl sulfate and povidone. In some cases, the milling, in addition to reducing the particle size of the abiraterone acetate, reduces the particle size of one or more components of the grinding matrix. Thus, in some cases, the milling reduces the particles of one or more of the materials (e.g., lactose) used as the millable grinding compound. In some cases, abiraterone acetate is milled with lactose (e.g., lactose monohydrate) and sodium lauryl sulfate. In some cases during dry milling the abiraterone acetate can be present at 20-60% (w/w) the lactose at up to 80% (w/w) the mannitol at up to 80% (w/w) and the povidone and sodium lauryl sulfate each (or both) at 1-10% (w/w).

In some embodiments, the abiraterone acetate is dry milled in the presence of one or more antioxidants and/or one or more sequestering agents (i.e., an agent that can sequester ions, e.g., metal ions) in addition to at least one millable grinding compound and at least one facilitating agent. Thus, one or more of: butylated hydroxyanisole (BHA), butylated hydroxytoluene (BHT), ascorbic acid, fumaric acid, tartaric acid and citric acid (e.g., anhydrous citric acid) or mixtures thereof can be present during the dry milling. In some cases, both at least one antioxidant and at least one sequestering agent are present during milling. During milling, the ascorbic acid, fumaric acid, tartaric acid and citric acid (e.g., anhydrous citric acid) can be present at 8% or less on a w/w basis (e.g., 7%-0.1%, 1%-0.1%, or 0.2% each or in combination) and the BHT and BHA can be present at 0.5% or less (e.g., 0.5%-0.01%, 0.2%-0.08%, 0.15%-0.05%, or 0.1% each or in combination). One or more additional antioxidants and/or one or more additional sequestering agents can be added to the milled material after milling is completed.

The pharmaceutical composition can be a unit dosage form such as a capsule or tablet containing 50-500 mg of abiraterone acetate (e.g., 50, 55, 60, 65, 70, 75, 80, 85, 90, 95, 100, 110, 115, 120, 125, 130, 135, 140, 145, 150, 175, 200, 225, 250, 275, 300, 325, 350, 375, 400, 425, 450, 475 or 500 mg), wherein the abiraterone acetate has a size profile described herein and/or the dosage form has a dissolution profile described herein.

Also described herein is a method for treating a patient comprising administering a daily dose of 1000 mg to 50 mg of abiraterone acetate (e.g., 900, 850, 800, 750, 700, 650, 600, 550, 525, 500, 475, 450, 425, 400, 375, 350, 325, 300, 275, 250, 225, 200, 150, 100, 90, 80, 70, 60, or 50 mg) in the form of a pharmaceutical composition described herein (e.g., by administering one or more units of a unit dosage form described herein comprising abiraterone acetate), wherein the abiraterone acetate has a size profile described herein and/or the dosage form has a dissolution profile described herein. The patient can also be treated with a glucocorticoid such as prednisone, prednisolone, or dexamethasone. Alternatively, the patient can also be treated with methylprednisolone, for example at 5-15 mg/day (e.g., 5, 6, 7, 8, 9, 10 mg/day, for example two 4 mg doses/day). In some cases a patient, e.g., a patient not suffering from hepatic impairment, is treated at 500 mg/daily by administering four 125 mg unit dosage forms of abiraterone acetate as described herein.

In some cases, for the dosage forms described herein, the $AUC_{0-\infty}$ for a single dose of a unit dosage form described herein (or an effective dose thereof, e.g., 4×125 mg) when administered with a low-fat meal (7% fat, 300 calories) is 4-fold or less (3-fold or less, 2-fold or less, 1.5-fold or less) higher than when administered in the fasted state.

In some cases, for the dosage forms described herein, the $AUC_{0-\infty}$ (or $AUC_{0-t}$) for a single dose of a unit dosage form described herein (or an effective dose thereof, e.g., 4×125 mg) when administered with a high-fat meal (57% fat, 825 calories) is 8-fold or less (7-fold or less, 5-fold or less, 3-fold or less, 2-fold or less, 1.5-fold or less) higher than when administered in the fasted state.

In some cases, for the dosage forms described herein, the Cmax for a single dose of a unit dosage form described herein (or an effective dose thereof, e.g., 4×125 mg) when administered with a high-fat meal (57% fat, 825 calories) is 15-fold or less (13-fold or less or, 12-fold or less, 11-fold or less, 10-fold or less, 9-fold or less, 8-fold or less, 7-fold or less, 6-fold or less, 5-fold or less) higher than when administered in the fasted state.

In some cases, for the dosage forms described herein, the Cmax for a single dose of a unit dosage form described herein (or an approved dose thereof, e.g., 4×125 mg) when administered with a low-fat meal (7% fat, 300 calories) is 6-fold or less (5-fold or less or 4-fold or less, 3-fold or less, 2-fold or less, 1.5-fold or less) higher than when administered in the fasted state.

The dissolution rate of a tablet containing 100 mg or 125 mg of abiraterone acetate when tested in 900 ml of pH 4.5 phosphate buffer with 0.1%-0.12% sodium lauryl sulfate (respectively) using USP Apparatus II at 75 rpm, is such that at least 90% or at least 95% of the abiraterone acetate dissolves in 20 min or less (e.g., 19 min or less, 18 min or less, 17 min or less, 16 min or less, 15 min or less, 14 min or less, 13 min or less, 11 min or less, 9 min or less). For example, 90% can dissolve in 9-19 minutes. In cases where the tablet contains more than 125 mg or less than 100 mg of abiraterone acetate, the dissolution rate given is for a fraction of a larger tablet (or multiple of a smaller tablet) providing 100-125 mg of abiraterone acetate. In some cases, at least 80% or at least 85% of the abiraterone acetate dissolves in 15 min or less (e.g., 14 min or less, 13 min or less, 12 min or less, 11 min or less, 10 min or less, 9 min or less, 8 min or less, or 7 min or less). For example, 85% can dissolve in 7-14 minutes.

In some cases, at least 80% or at least 85% of the abiraterone acetate in a 125 mg unit dosage form dissolves in 15 min or less (e.g., 14 min or less, 13 min or less, 12 min or less, 11 min or less, 10 min or less, 9 min or less, 8 min or less, or 7 min or less) after storage at 4 weeks or more (e.g., 8 weeks or 12 weeks) at 25° C. at 60% RH. In some cases, at least 95% of the abiraterone acetate dissolves in 15 min or less (e.g., 14 min or less, 13 min or less, 11 min or less, 9 min or less) after storage at 3 weeks or more (e.g., 6 weeks or 9 weeks) at 40° C. at 75% RH. For example, 95% can dissolve in 8-14 min. Here too, in cases where the tablet contains more than 125 mg or less than 100 mg of abiraterone acetate, the dissolution rate given is for a fraction of a larger tablet (or multiple of a smaller tablet) providing 100-125 mg of abiraterone acetate.

In certain embodiments, the coefficient of variation observed for a pharmaceutical composition described herein in one or more of Cmax, AUC(0-t), and AUC(0-∞) will be less than 60%, less than 50%, less than 40%, less than 30%, less than 25%, or less than 20% when administered to healthy patients in the fasted state. In some embodiments, a pharmaceutical composition described herein (125 mg unit dosage form or a 500 mg dose of a unit dosage form, e.g., 4×125 mg) shows less variability in one or more of Cmax, AUC(0-t), and AUC(0-∞) relative to, e.g., a 250 mg dosage form of Zytiga® (or a 1000 dose of a a 250 mg dosage form of Zytiga®) in comparative pharmacokinetic testing.

In some cases, the hardness of abiraterone tablets is between 100N and 190N (e.g., 110N to 180N).

The drug product intermediate can be prepared by dry milling the following materials: (A) abiraterone acetate at 5-60 weight percent, lactose (e.g., lactose monohydrate) at 30-95 weight percent, sodium lauryl sulfate at 0.1-15 weight percent; BHA at 0.001-1 weight percent, and BHT at 0.001-1 weight percent; (B) abiraterone acetate at 10-50 weight percent, lactose (e.g., lactose monohydrate) at 40-80 weight percent, sodium lauryl sulfate at 0.5-10 weight percent; BHA at 0.01-0.8 weight percent, and BHT at 0.01-0.8 weight percent; (C) abiraterone acetate at 20-40 weight percent, lactose (e.g., lactose monohydrate) at 50-70 weight percent, sodium lauryl sulfate at 2-8 weight percent; BHA at 0.05-0.5 weight percent, and BHT at 0.05-0.5 weight percent; (D) abiraterone acetate at 25-35 weight percent, lactose (e.g., lactose monohydrate) at −60-70 weight percent, sodium lauryl sulfate at 4-8 weight percent; BHA at 0.05-0.15 weight percent, and BHT at 0.05-0.15 weight percent; and (E) abiraterone acetate at 30 weight percent, lactose (e.g., lactose monohydrate) at 63.8 weight percent, sodium lauryl sulfate at 6 weight percent; BHA at 0.1 weight percent, and BHT at 0.1 weight percent.

Drug product intermediate described above can be processed into tablets having the following materials: (A) abiraterone acetate at 5-50 weight percent, lactose (e.g., lactose monohydrate) at 5-80 weight percent, sodium lauryl sulfate at 0.1-10 weight percent, BHA at 0.001-1 weight percent, BHT at 0.001-1 weight percent, microcrystalline cellulose at 5-80 weight percent croscarmellose sodium at 0.5-20 weight percent, and sodium stearyl fumarate at 0.01-10 weight percent; (B) abiraterone acetate at 8-40 weight percent, lactose (e.g., lactose monohydrate) at 10-60 weight percent, sodium lauryl sulfate at 0.5-8 weight percent, BHA at 0.01-0.05 weight percent, BHT at 0.01-0.5 weight percent, microcrystalline cellulose at 10-70 weight percent, croscarmellose sodium at 1-15 weight percent, and sodium stearyl fumarate at 0.05-5 weight percent; (C) abiraterone acetate at 10-30 weight percent, lactose (e.g., lactose monohydrate) at 20-40 weight percent, sodium lauryl sulfate at 1-5 weight percent; BHA at 0.01-0.2 weight percent, BHT at 0.01-0.2 weight percent, microcrystalline cellulose at 20-60 weight percent, croscarmellose sodium at 2-10 weight percent, and sodium stearyl fumarate at 0.1-2 weight percent; (D) abiraterone acetate at 12-17 weight percent, lactose (e.g., lactose monohydrate) at 25-35 weight percent, sodium lauryl sulfate at 2-5 weight percent; BHA at 0.01-0.2 weight percent, BHT at 0.01-0.2 weight percent, microcrystalline cellulose at 35-50 weight percent, croscarmellose sodium at 5-9 weight percent, and sodium stearyl fumarate at 0.2-0.8 weight percent; and (E) abiraterone acetate at 14.29 weight percent, lactose (e.g., lactose monohydrate) at 30.38 weight percent, sodium lauryl sulfate at 3.21 weight percent; BHA at 0.05 weight percent, BHT at 0.05 weight percent, microcrystalline cellulose at 44-53 weight percent, croscarmellose sodium at 7 weight percent, and sodium stearyl fumarate at 0.5 weight percent.

In some embodiments, the dry milling apparatus used to dry mill abiraterone acetate is a mill selected from the group consisting of: attritor mills (horizontal or vertical), nutating mills, tower mills, pearl mills, planetary mills, vibratory mills, eccentric vibratory mills, gravity-dependent-type ball mills, rod mills, roller mills and crusher mills. In some embodiments, the dry milling apparatus used to dry mill abiraterone acetate is a mill selected from the group consisting of: jet mills, spiral jet mills, micronisers or pulverizers. Preferably, the method is configured to produce the abiraterone acetate in a swing batch or continuous fashion.

In some embodiments, where a mill uses milling bodies, the milling bodies within the milling apparatus are mechanically agitated by 1, 2 or 3 rotating shafts. The milling bodies can be formed of a material selected from the group consisting of: ceramics, glasses, steels, polymers, ferromagnetics and metals and other suitable materials. In some embodiments, the milling bodies are steel balls having a diameter selected from the group consisting of: between 1 and 20 mm, between 2 and 15 mm and between 3 and 10 mm. In various embodiments of the dry milling method, the milling bodies are zirconium oxide balls having a diameter selected from the group consisting of: between 1 and 20 mm, between 2 and 15 mm and between 3 and 10 mm.

In another embodiment, the milling time period is a range selected from the group consisting of: between 10 minutes and 6 hours, between 10 minutes and 2 hours, between 10 minutes and 90 minutes, between 10 minutes and 1 hour, between 10 minutes and 45 minutes, between 10 minutes and 30 minutes, between 5 minutes and 30 minutes, between 5 minutes and 20 minutes, between 2 minutes and 10 minutes, between 2 minutes and 5 minutes, between 1 minutes and 2 minutes.

Additional Milling Matrixes and Facilitating Agents

In embodiments, the grinding matrix is a single material or is a mixture of two or more materials in any proportion. In some embodiments, the single material or a mixture of two or more materials is selected from the group consisting of: mannitol, sorbitol, isomalt, xylitol, maltitol, lactitol, erythritol, arabitol, ribitol, glucose, fructose, mannose, galactose, anhydrous lactose, lactose monohydrate, sucrose, maltose, trehalose, and maltodextrins. In some embodiments the single material or mixture of two or more materials is selected from the group consisting of: dextrin, inulin, dextrates, polydextrose, starch, wheat flour, corn flour, rice flour, rice starch, tapioca flour, tapioca starch, potato flour, potato starch, other flours and starches, milk powder, skim milk powders, other milk solids and derivatives, soy flour, soy meal or other soy products, cellulose, microcrystalline cellulose, microcrystalline cellulose based co-blended materials, pregelatinized (or partially gelatinized) starch, hypromellose, carboxymethyl cellulose, hydroxypropyl cellulose, citric acid, tartaric acid, malic acid, maleic acid, fumaric acid, ascorbic acid, succinic acid, sodium citrate, sodium tartrate, sodium malate, sodium ascorbate, potassium citrate, potassium tartrate, potassium malate, sodium acetate, potassium ascorbate, sodium carbonate, potassium carbonate, magnesium carbonate, sodium bicarbonate, potassium bicarbonate, calcium carbonate, dibasic calcium phosphate, tribasic calcium phosphate, sodium sulfate, sodium chloride, sodium metabisulphite, sodium thiosulfate, ammonium chloride, glauber's salt, ammonium carbonate, sodium bisulfate, magnesium sulfate, potash alum, potassium chloride, sodium hydrogen sulfate, sodium hydroxide, crystalline hydroxides, hydrogen carbonates, ammonium chloride, methylamine hydrochloride, ammonium bromide, silica, thermal silica, alumina, titanium dioxide, talc, chalk, mica, kaolin, bentonite, hectorite, magnesium trisilicate, clay based materials or aluminium silicates, sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, cetrimonium bromide, cetrimonium chloride, cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, sucrose palmitate, sucrose stearate, sucrose distearate, sucrose laurate, glycocholic acid, sodium glycholate, cholic acid, sodium cholate, sodium deoxycholate, deoxycholic acid, sodium taurocholate, taurocholic acid, sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, calcium dodecylbenzene sulfonate, sodium dodecylbenzene sulfonate, diisopropyl naphthaenesulphonate, erythritol distearate, naphthalene sulfonate formaldehyde condensate, nonylphenol ethoxylate (poe-30), tristyrylphenol ethoxylate, polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, sodium methyl naphthalene formaldehyde sulfonate, sodium n-butyl naphthalene sulfonate, tridecyl alcohol ethoxylate (poe-18), triethanolamine isodecanol phosphate ester, triethanolamine tristyrylphosphate ester, tristyrylphenol ethoxylate sulfate, bis(2-hydroxyethyl)tallowalkylamines.

In some embodiments, the concentration of the single (or first) component of the grinding matrix is selected from the group consisting of: 5-99% w/w, 10-95% w/w, 15-85% w/w, of 20-80% w/w, 25-75% w/w, 30-60% w/w, 40-50% w/w. In some embodiments, the concentration of the second or subsequent component of the grinding matrix is selected from the group consisting of: 5-50% w/w, 5-40% w/w, 5-30% w/w, of 5-20% w/w, 10-40 w/w, 10-30% w/w, 10-20% w/w, 20-40% w/w, or 20-30% w/w or if the second or subsequent material is a surfactant or water soluble polymer the concentration is selected from 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1% w/w, of 0.75-1.25% w/w, 0.75-1% and 1% w/w.

In some embodiments, abiraterone acetate is milled in the presence of:
(a) Lactose monohydrate or lactose monohydrate combined with at least one material selected from the group consisting of: xylitol; lactose anhydrous; microcrystalline cellulose; sucrose; glucose; sodium chloride; talc; kaolin; calcium carbonate; malic acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl) tallowalkylamines.
(b) Lactose anhydrous or lactose anhydrous combined with at least one material selected from the group consisting of: lactose monohydrate; xylitol; microcrystalline cellulose; sucrose; glucose; sodium chloride; talc; kaolin; calcium carbonate; malic acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/Lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl) tallowalkylamines.

(c) Mannitol or mannitol combined with at least one material selected from the group consisting of: lactose monohydrate; xylitol; lactose anhydrous; microcrystalline cellulose; sucrose; glucose; sodium chloride; talc; kaolin; calcium carbonate; malic acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl) tallowalkylamines.

(d) Sucrose or sucrose combined with at least one material selected from the group consisting of: lactose monohydrate; lactose anhydrous; mannitol; microcrystalline cellulose; glucose; sodium chloride; talc; kaolin; calcium carbonate; malic acid; tartaric acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl) tallowalkylamines.

(e) Glucose or glucose combined with at least one material selected from the group consisting of: lactose monohydrate; lactose anhydrous; mannitol; microcrystalline cellulose; sucrose; sodium chloride; talc; kaolin; calcium carbonate; malic acid; tartaric acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and polyoxyl 100 stearyl ether, sodium lauryl sulfate and poloxamer 407, sodium lauryl sulfate and Poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl) tallowalkylamines.

(f) Sodium chloride or sodium chloride combined with at least one material selected from the group consisting of: lactose monohydrate; lactose anhydrous; mannitol; microcrystalline cellulose; sucrose; glucose; talc;

kaolin; calcium carbonate; malic acid; tartaric acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde Sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl) tallowalkylamines.

(g) Xylitol or xylitol combined with at least one material selected from the group consisting of: lactose monohydrate; lactose anhydrous; mannitol; microcrystalline cellulose; sucrose; glucose; sodium chloride; talc; kaolin; calcium carbonate; malic acid; tartaric acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl) tallowalkylamines.

(h) Tartaric acid or tartaric acid combined with at least one material selected from the group consisting of: lactose monohydrate; lactose anhydrous; mannitol; microcrystalline cellulose; sucrose; glucose; sodium chloride; talc; kaolin; calcium carbonate; malic acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and Polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; Phosphate Esters, tristyrylphenol Ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl) tallowalkylamines.

(i) Microcrystalline cellulose or microcrystalline cellulose combined with at least one material selected from the group consisting of: lactose monohydrate; xylitol; lactose anhydrous; mannitol; sucrose; glucose; sodium chloride; talc; kaolin; calcium carbonate; malic acid; tartaric acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and Polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched);

diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl)tallowalkylamines.

(j) Kaolin combined with at least one material selected from the group consisting of: lactose monohydrate; xylitol; lactose anhydrous; mannitol; microcrystalline cellulose; sucrose; glucose; sodium chloride; talc; kaolin; calcium carbonate; malic acid; tartaric acid; trisodium citrate dihydrate; D,L-malic acid; sodium pentane sulfate; sodium octadecyl sulfate; Polyoxyl 100 stearyl ether; Polyoxyl 10 stearyl ether; sodium n-lauroyl sacrosine; lecithin; docusate sodium; polyoxyl-40-stearate; Hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; briethanolamine tristyrylphosphate ester; tristyrylphenol ethoxylate sulfate; bis(2-hydroxyethyl) tallowalkylamines.

(k) Talc combined with at least one material selected from the group consisting of: lactose monohydrate; xylitol; lactose anhydrous; mannitol; microcrystalline cellulose; sucrose; glucose; sodium chloride; kaolin; calcium carbonate; malic acid; tartaric acid; trisodium citrate dihydrate; D,L-malic acid; sodium pentane sulfate; sodium octadecyl sulfate; polyoxyl 100 stearyl ether; polyoxyl 10 stearyl ether; sodium n-lauroyl sacrosine; lecithin; docusate sodium; polyoxyl-40-stearate; hydrophobic collodial silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulfate and PEG 6000, sodium lauryl sulfate and PEG 8000, sodium lauryl sulfate and PEG 10000, sodium lauryl sulfate and polyoxyl 100 stearyl ether, sodium lauryl sulfate and poloxamer 407, sodium lauryl sulfate and poloxamer 338, sodium lauryl sulfate and poloxamer 188; poloxamer 407, poloxamer 338, poloxamer 188, alkyl naphthalene sulfonate condensate/lignosulfonate blend; calcium dodecylbenzene sulfonate (branched); diisopropyl naphthalenesulphonate; erythritol distearate; linear and branched dodecylbenzene sulfonic acids; naphthalene sulfonate formaldehyde condensate; nonylphenol ethoxylate, POE-30; phosphate esters, tristyrylphenol ethoxylate, free acid; polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; sodium methyl naphthalene; formaldehyde sulfonate; sodium salt of n-butyl naphthalene sulfonate; tridecyl alcohol ethoxylate, POE-18; triethanolamine isodecanol phosphate ester; triethanolamine tristyrylphosphate ester; tristyrylphenol ethoxylate sulfate; bis(2-hydroxyethyl) tallowalkylamines.

In some embodiments, the abiraterone acetate is dry milled with one or more additional materials is selected from the group consisting of: a material considered to be 'Generally Regarded as Safe' (GRAS) for pharmaceutical products.

In some embodiments, the dry milling of abiraterone acetate takes place in the presence of a facilitating agent or combination of facilitating agents. In some embodiments, the facilitating agent is selected from the group consisting of: a glidant, a surfactant, a polymer, and/or a lubricant. In some embodiments, the facilitating agent is selected from the group consisting of: colloidal silicon dioxide, sodium stearate and talc. In some embodiments, the facilitating agent is selected from the group consisting of: benzethonium chloride, docusate sodium, polyethylene alkyl ethers, sodium lauryl sulfate, tricaprylin, alpha tocopherol, glyceryl monooleate, myristyl alcohol, poloxamer, polyoxyethylene alkyl ethers, polyoxyethylene stearates, polyoxyethylene castor oil derivatives, polyoxyl 15 hydroxystearate, polyoxylglycerides, polysorbates, propylene glycol dilaurate, sorbitan esters, sucrose palmitate, vitamin E polyethylene glycol succinate, polyethylene glycols (PEG), poloxamers, poloxamines, sarcosine based surfactants, polysorbates, aliphatic alcohols, alkyl and aryl sulfates, alkyl and aryl polyether sulfonates and other sulfate surfactants, trimethyl ammonium based surfactants, lecithin and other phospholipids, bile salts, polyoxyethylene castor oil derivatives, polyoxyethylene sorbitan fatty acid esters, sorbitan fatty acid esters sucrose fatty acid esters, alkyl glucopyranosides, alkyl maltopyranosides, glycerol fatty acid esters, alkyl benzene sulphonic acids, alkyl ether carboxylic acids, alkyl and aryl phosphate esters, alkyl and aryl sulfate esters, alkyl and aryl sulphonic acids, alkyl phenol phosphates esters, alkyl phenol sulfates esters, alkyl and aryl phosphates, alkyl polysaccharides, alkylamine ethoxylates, alkyl-naphthalene sulphonates formaldehyde condensates, sulfosuccinates, lignosulfonates, ceto-oleyl alcohol ethoxylates, condensed naphthalene sulphonates, dialkyl and alkyl naphthalene sulphonates, di-alkyl sulphosuccinates, ethoxylated nonylphenols, ethylene glycol esters, fatty alcohol alkoxylates, hydrogenated tallowalkylamines, mono-alkyl sulphosuccinamates, nonyl phenol ethoxylates, sodium oleyl N-methyl taurate, tallowalkylamines, linear and branched dodecylbenzene sulfonic acids.

In some embodiments, the facilitating agent is selected from the group consisting of sodium stearyl sulfate, sodium stearyl fumarate, magnesium stearate, talc, myristic acid, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, cetyl trimethylammonium bromide, cetyl trimethylammonium chloride, cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, sucrose palmitate, sucrose stearate, sucrose distearate, sucrose laurate, glycocholic acid, sodium glycholate, cholic acid, sodium cholate, sodium deoxycholate, deoxycholic acid, sodium taurocholate, taurocholic acid, sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/lignosulfonate blend, calcium dodecylbenzene sulfonate, sodium dodecylbenzene sulfonate, diisopropyl naphthaenesulphonate, erythritol distearate, naphthalene sulfonate formaldehyde condensate, nonylphenol ethoxylate (POE-30), tristyrylphenol ethoxylate, polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, sodium methyl naphthalene formaldehyde sulfonate, sodium n-butyl naphthalene sulfonate, tridecyl alcohol ethoxylate (poe-18), triethanolamine isodecanol phosphate ester, triethanolamine tristyrylphosphate ester, tristyrylphenol ethoxylate sulfate, bis(2) hydroxyethyl)tallowalkylamines.

In some embodiments the facilitating agent is selected from the list of: polyvinylpyrrolidones (PVP), polyvinylalcohol, acrylic acid based polymers and copolymers of acrylic acid.

In some embodiments, the facilitating agent has a concentration during dry milling selected from the group consisting of: 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1% w/w, of 0.75-1.25% w/w, 0.75-1% and 1% w/w.

In some embodiments, a facilitating agent is used or combination of facilitating agents is used during dry milling. In some embodiments, the facilitating agent is added during dry milling. In some embodiments, the facilitating agent is added to the dry milling at a time selected from the group consisting of: with 1-5% of the total milling time remaining, with 1-10% of the total milling time remaining, with 1-20% of the total milling time remaining, with 1-30% of the total milling time remaining, with 2-5% of the total milling time remaining, with 2-10% of the total milling time remaining, with 5-20% of the total milling time remaining and with 5-20% of the total milling time remaining.

The reasons for including facilitating agents include, but are not limited to providing better dispersibility, control of agglomeration, the release or retention of the active particles from the delivery matrix. Examples of facilitating agents include, but are not limited to: sodium lauryl sulfate, cross-linked PVP (crospovidone), cross linked sodium carboxymethylcellulose (croscarmellose sodium), sodium starch glycolate, povidone (PVP), povidone K12, povidone K17, povidone K25, povidone K29/32 and povidone K30, stearic acid, magnesium stearate, calcium stearate, sodium stearyl fumarate, sodium stearyl lactylate, zinc stearate, sodium stearate or lithium stearate, other solid state fatty acids such as oleic acid, lauric acid, palmitic acid, erucic acid, behenic acid, or derivatives (such as esters and salts), amino acids such as leucine, isoleucine, lysine, valine, methionine, phenylalanine, aspartame or acesulfame K.

In another aspect the disclosure includes a method of treating a human in need of such treatment comprising the step of administering to the human an effective amount of a pharmaceutical composition as described herein for treatment of castration resistant prostate cancer. The treatment can include administering 500 mg of abiraterone acetate daily (e.g., in 1 or 2 or 4 equal doses (e.g., one unit dose containing 500 mg, two unit doses containing 250 mg of abiraterone acetate each, or four unit doses containing 125 mg of abiraterone acetate each). The patient can also be treated with a glucocorticoid, e.g., prednisone, dexamethasone or prednisolone (e.g., at 5 mg, twice daily). Alternatively, the patient can be treated with methylprednisolone (e.g. at 4 mg twice daily). The patient can also be treated with other chemotherapeutic agents or other agents for the treatment of cancer (e.g., prostate cancer).

The disclosure also includes a method for treating breast cancer (e.g., metastatic breast cancer) and ovarian cancer (e.g., epithelial ovarian cancer) using a composition described herein.

In another aspect, the disclosure comprises the use of a pharmaceutical composition as described herein in the manufacture of a medicament for the treatment of a human in need of such treatment.

In another aspect the disclosure comprises a method for manufacturing a pharmaceutical composition as described herein comprising the step of combining a composition comprising abiraterone acetate prepared by a method described herein or a composition as described herein, together with one of a diluent, lubricant, excipient, disintegrant, wetting agent, to produce a pharmaceutically acceptable dosage form.

The disclosure described herein may include one or more ranges of values (e.g. size, concentration etc.). A range of values will be understood to include all values within the range, including the values defining the range, and values adjacent to the range that lead to the same or substantially the same outcome as the values immediately adjacent to that value which defines the boundary to the range.

The entire disclosures of all publications (including patents, patent applications, journal articles, laboratory manuals, books, or other documents) cited herein are hereby incorporated by reference. Inclusion does not constitute an admission is made that any of the references constitute prior art or are part of the common general knowledge of those working in the field to which this disclosure relates.

Throughout this specification, unless the context requires otherwise, the word "comprise" or variations, such as "comprises" or "comprising" will be understood to imply the inclusion of a stated integer, or group of integers, but not the exclusion of any other integers or group of integers. It is also noted that in this disclosure, and particularly in the claims and/or paragraphs, terms such as "comprises", "comprised", "comprising" and the like can have the meaning attributed to it in US Patent law; e.g., they can mean "includes", "included", "including", and the like.

"Therapeutically effective amount" as used herein with respect to methods of treatment and in particular drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

Throughout this specification, unless the context requires otherwise, the phrase "dry mill" or variations, such as "dry milling," should be understood to refer to milling in at least the substantial absence of liquids. If liquids are present, they are present in such amounts that the contents of the mill retain the characteristics of a dry powder.

The term "millable" means that the grinding matrix is capable of being reduced in size under the dry milling conditions of the method of the disclosure. In one embodiment of the disclosure, the milled grinding matrix is of a comparable particle size to the abiraterone acetate. In another embodiment of the disclosure the particle size of the matrix is substantially reduced but not as small as the abiraterone acetate.

Those skilled in the art will appreciate that the disclosure described herein is susceptible to variations and modifications other than those specifically described. It is to be understood that the disclosure includes all such variations and modifications. The disclosure also includes all of the steps, features, compositions and materials referred to or indicated in the specification, individually or collectively and any and all combinations or any two or more of the steps or features.

The present disclosure is not to be limited in scope by the specific embodiments described herein, which are intended for the purpose of exemplification only. Functionally equivalent products, compositions and methods are clearly within the scope of the disclosure as described herein.

Other aspects and advantages of the disclosure will become apparent to those skilled in the art from a review of the ensuing description.

DRAWINGS

DETAILED DESCRIPTION OF THE DISCLOSURE

Particle Size

Figure 1:
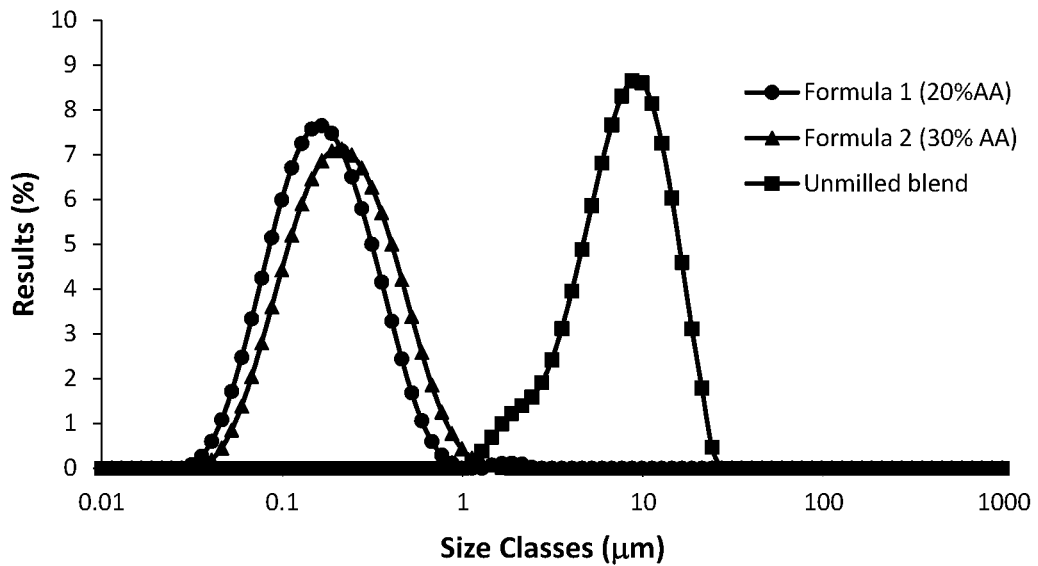
FIG. 1 is a graph of the results of particle size analysis of unmilled abiraterone acetate and abiraterone acetate in formula 1 and formula 2 of Example 1.

For measurements made using a laser diffraction the term "median particle size" is defined as the median particle diameter as determined on an equivalent spherical particle volume basis. Where the term median is used, it is understood to describe the particle size that divides the population in half such that 50% of the population on a volume basis is greater than or less than this size. The median particle size is written as: $[D_{50}]$ or $D_{[50]}$ or [D50], D50, D(0.50) or D[0.5] or similar. As used herein $[D_{50}]$ or $D_{[50]}$ or [D50], D50, D(0.50) or D[0.5] or similar shall be taken to mean median particle size.

The term "Dx of the particle size distribution" refers to the xth percentile of the distribution on a volume basis; thus, D90 refers to the $90^{th}$ percentile, D95 refers to the $95^{th}$ percentile, and so forth. Taking D90 as an example this can often be written as, [D90] or $D_{[90]}$ or [D90], D(0.90) or D[0.9] or similar. With respect to the median particle size and Dx an upper case D or lowercase d are interchangeable and have the same meaning. Another commonly used way of describing a particle size distribution measured by laser diffraction, or an equivalent method known in the art, is to describe what % of a distribution is under or over a nominated size. The term "percentage less than" also written as "%<" is defined as the percentage, by volume, of a particle size distribution under a nominated size—for example the %<1000 nm. The term "percentage greater than" also written as "%>" is defined as the percentage, by volume, of a particle size distribution over a nominated size—for example the %>1000 nm. The term D(3,2) is referred to as the area-weighted mean size or the Sauter diameter; the term D(4,3) is referred to as the volume-weighted mean size. Detailed descriptions of how these values are calculated are known in the art and can be found in, for example, ISO 9276-2:2014(E).

For many of the materials subject to the methods of this disclosure the particle size can be easily measured. Where the active material has poor water solubility and the matrix it is milled in has good water solubility the powder can simply be dispersed in an aqueous solvent. In this scenario the matrix dissolves leaving the active material dispersed in the solvent. This suspension can then be measured by techniques such as PCS or laser diffraction.

Suitable methods to measure an accurate particle size where the active material has substantive aqueous solubility or the matrix has low solubility in a water based dispersant are outlined below.

1. In the circumstance where an insoluble matrix such as microcrystalline cellulose prevents the measurement of the active material separation techniques such as filtration or centrifugation could be used to separate the insoluble matrix from the active material particles. Other ancillary techniques would also be required to determine if any active material was removed by the separation technique so that this could be taken into account.
2. In the case where the active material is too soluble in water, other solvents could be evaluated for the measurement of particle size. Where a solvent could be found that active material is poorly soluble in but is a good solvent for the matrix a measurement would be relatively straight forward. If such a solvent is difficult to find another approach would be to measure the ensemble of matrix and active material in a solvent (such as iso-octane) which both are insoluble in. Then the powder would be measured in another solvent where the active material is soluble but the matrix is not. Thus with a measurement of the matrix particle size and a measurement of the size of the matrix and active material together an understanding of the active material particle size can be obtained.

3. In some circumstances image analysis could be used to obtain information about the particle size distribution of the active material. Suitable image measurement techniques might include transmission electron microscopy (TEM), scanning electron microscopy (SEM), optical microscopy and confocal microscopy. In addition to these standard techniques some additional technique would be required to be used in parallel to differentiate the active material and matrix particles. Depending on the chemical makeup of the materials involved possible techniques could be elemental analysis, Raman spectroscopy, FTIR spectroscopy or fluorescence spectroscopy.

Improving the Dissolution Profile

The process results in the abiraterone acetate having an improved dissolution profile. An improved dissolution profile has significant advantages including, in some cases, the improvement of bioavailability of the abiraterone acetate in vivo. Standard methods for determining the dissolution profile of a material in vitro are available in the art. A suitable method to determine an improved dissolution profile in vitro may include determining the concentration of the sample material in a solution over a period of time and comparing the results from the sample material to a control sample. An observation that peak solution concentration for the sample material was achieved in less time than the control sample would indicate that the sample material has an improved dissolution profile. The test sample can be the unit dosage form containing abiraterone acetate with grinding matrix and/or other additives that has been subject to the processes of the disclosure described here, as well as excipients to manufacture the final dosage form. Herein a control sample can be as a physical of the components in the measurement sample with the same relative proportions of active, matrix and/or additive as the measurement sample. The control sample can also be the commercially available dosage form, Zytiga® tablets, cut to represent an equivalent quantity of abirateratone acetate as the test sample. Standard methods for determining the improved dissolution profile of a material in vivo are available in the art.

Crystallization Profile

Methods for determining the crystallinity profile of the abiraterone acetate are widely available in the art. Suitable methods may include X-ray diffraction, differential scanning calorimetry, and Raman or IR spectroscopy.

Amorphicity Profile

Methods for determining the amorphous content of the abiraterone acetate are widely available in the art. Suitable methods may include X-ray diffraction, differential scanning calorimetry, and Raman or IR spectroscopy.

Grinding Matrix

As will be described subsequently, selection of an appropriate grinding matrix affords particular advantageous applications of the method of the present disclosure. Again, as will be described subsequently, a highly advantageous aspect of the present disclosure is that certain grinding matrixes appropriate for use in the method of the disclosure are also appropriate for use in a medicament. The present disclosure encompasses methods for the production of a medicament incorporating both the abiraterone acetate and the grinding matrix or in some cases the abiraterone acetate and a portion of the grinding matrix, medicaments so produced, and methods of treatment using the medicament. The medicament may include only the milled abiraterone acetate together with the milled grinding matrix or, more preferably, the milled abiraterone acetate and milled grinding matrix may be combined with one or more pharmaceutically acceptable carriers, as well as any desired excipients or other like agents commonly used in the preparation of medicaments.

In some cases at least one component of the grinding matrix is harder than the abiraterone acetate, and is thus capable of reducing the particle size of the abiraterone acetate under the dry milling conditions of the disclosure. Again without wishing to be bound by theory, under these circumstances it is believed that the millable grinding matrix affords the advantage of the present disclosure through a second route, with the smaller particles of grinding matrix produced under the dry milling conditions enabling greater interaction with the abiraterone acetate. The quantity of the grinding matrix relative to the quantity of abiraterone acetate, and the extent of physical degradation of the grinding matrix, is sufficient to inhibit re-agglomeration of the particles of the active material In some embodiments, the quantity of the grinding matrix relative to the quantity of abiraterone acetate, and the extent of size reduction of the grinding matrix, is sufficient to inhibit re-agglomeration of the particles of the active material. As detailed above, the grinding matrix can include one or more anti-oxidants and/or one or more sequestering agents.

In some embodiments, the grinding matrix has a low tendency to agglomerate during dry milling. While it is difficult to objectively quantify the tendency to agglomerate during milling, it is possible to obtain a subjective measure by observing the level of "caking" of the grinding matrix in the milling chamber of the mill as dry milling progresses.

The grinding matrix may be an inorganic or organic substance.

Milling Bodies

In the method of the present disclosure, where milling bodies are utilized, the milling bodies are preferably chemically inert and rigid. The term "chemically-inert", as used herein, means that the milling bodies do not react chemically with the abiraterone acetate or the grinding matrix.

As described above, the milling bodies are essentially resistant to fracture and erosion in the milling process.

The milling bodies are desirably provided in the form of bodies which may have any of a variety of smooth, regular shapes, flat or curved surfaces, and lacking sharp or raised edges. For example, suitable milling bodies can be in the form of bodies having ellipsoidal, ovoid, spherical or right cylindrical shapes. In some embodiments, the milling bodies are provided in the form of one or more of beads, balls, spheres, rods, right cylinders, drums or radius-end right cylinders (i.e., right cylinders having hemispherical bases with the same radius as the cylinder).

Depending on the nature of the abiraterone acetate and the grinding matrix, the milling bodies desirably have an effective mean diameter between about 0.1 and 30 mm, more preferably between about 1 and about 15 mm, still more preferably between about 3 and 10 mm.

The milling bodies may comprise various substances such as ceramic, glass, metal or polymeric compositions, in a particulate form. Suitable metal milling bodies are typically spherical and generally have good hardness (i.e. RHC 60-70), roundness, high wear resistance, and narrow size distribution and can include, for example, balls fabricated from type 52100 chrome steel, type 304, 316 or 440C stainless steel or type 1065 high carbon steel.

Ceramics, for example, can be selected from a wide array of ceramics desirably having sufficient hardness and resistance to fracture to enable them to avoid being chipped or crushed during milling and also having sufficiently high density. Suitable densities for milling bodies can range from about 1 to 15 g/cm$^3$, preferably from about 1 to 8 g/cm$^3$. Ceramics can be selected from steatite, aluminum oxide, zirconium oxide, zirconia-silica, yttria-stabilized zirconium oxide, magnesia-stabilized zirconium oxide, silicon nitride, silicon carbide, cobalt-stabilized tungsten carbide, and the like, as well as mixtures thereof.

Glass milling bodies are spherical (e.g. beads), have a narrow size distribution, are durable, and include, for example, lead-free soda lime glass and borosilicate glass. Polymeric milling bodies are preferably substantially spherical and can be selected from a wide array of polymeric resins having sufficient hardness and friability to enable them to avoid being chipped or crushed during milling, abrasion-resistance to minimize attrition resulting in contamination of the product, and freedom from impurities such as metals, solvents, and residual monomers.

Milling bodies can be formed from polymeric resins. Polymeric resins, for example, can be selected from cross-linked polystyrenes, such as polystyrene crosslinked with divinylbenzene, styrene copolymers, polyacrylates such as polymethylmethacrylate, polycarbonates, polyacetals, vinyl chloride polymers and copolymers, polyurethanes, polyamides, high density polyethylenes, polypropylenes, and the like. The use of polymeric milling bodies to grind materials down to a very small particle size (as opposed to mechanochemical synthesis) is disclosed, for example, in U.S. Pat. Nos. 5,478,705 and 5,500,331. Polymeric resins typically can have densities ranging from about 0.8 to 3.0 g/cm$^3$. Higher density polymeric resins are generally preferred. Alternatively, the milling bodies can be composite bodies comprising dense core bodies having a polymeric resin adhered thereon. Core particles can be selected from substances known to be useful as milling bodies, for example, glass, alumina, zirconia silica, zirconium oxide, stainless steel, and the like. Core substances have densities greater than about 2.5 g/cm$^3$.

In one embodiment of the disclosure, the milling bodies are formed from a ferromagnetic substance, thereby facilitating removal of contaminants arising from wear of the milling bodies by the use of magnetic separation techniques.

Each type of milling body has its own advantages. For example, metals have the highest specific gravities, which increase grinding efficiency due to increased impact energy. Metal costs range from low to high, but metal contamination of final product can be an issue. Glasses are advantageous from the standpoint of low cost and the availability of small bead sizes as low as 0.004 mm. However, the specific gravity of glasses is lower than other bodies and significantly more milling time is required. Finally, ceramics are advantageous from the standpoint of low wear and contamination, ease of cleaning, and high hardness.

Dry Milling

In the dry milling process of the present disclosure, the abiraterone acetate and grinding matrix, in the form of crystals, powders, or the like, are combined in suitable proportions with or without a plurality of milling bodies in a milling chamber that is mechanically agitated for a predetermined period of time at a predetermined intensity of agitation. Typically, a milling apparatus is used to impart motion to contents of the mill including any milling bodies by the external application of agitation, a stream of dry gas or other force, whereby various translational, rotational or inversion motions or combinations thereof are applied to the milling chamber and its contents, or by the internal application of agitation through a rotating shaft terminating in a blade, propeller, impeller or paddle or by a combination of both actions.

During milling, motion imparted to the milling bodies or gas flowing through the milling system can result in application of shearing forces as well as multiple impacts or collisions having significant intensity between the mill components, any milling bodies utilized and the particles of abiraterone acetate and the grinding matrix. The nature and intensity of the forces applied to the abiraterone acetate and the grinding matrix is influenced by a wide variety of processing parameters including: the type of milling apparatus; the intensity of the forces generated, the kinematic aspects of the process; the size, density, shape, and composition of any milling bodies used; the weight ratio of the abiraterone acetate and grinding matrix mixture to any milling bodies used; the duration of milling; the physical properties of both the abiraterone acetate and the grinding matrix; the atmosphere present during milling; and other factors.

Advantageously, the mill is capable of repeatedly or continuously applying mechanical compressive forces and shear stress to the abiraterone acetate and the grinding matrix. Throughout the remainder of the specification reference will be made to dry milling being carried out by way of a ball mill. Examples of this type of mill are attritor mills, nutating mills, tower mills, planetary mills, vibratory mills, gravity-dependent-type ball mills, jet mills, rod mills, roller mills or crusher mills, jet mills and pulverizing mills. It will be appreciated that dry milling in accordance with the method of the disclosure may also be achieved by any suitable milling method or means.

In some cases, the particle size of the abiraterone acetate prior to dry milling according to the methods described herein is less than about 1000 μm, as determined by sieve analysis. If the particle size of the abiraterone acetate is greater than about 1000 μm, then it is preferred that the particles of the abiraterone acetate substrate be reduced in size to less than 1000 μm using another particle size reduction method prior to dry milling according to the methods described herein.

Agglomerates of Abiraterone Acetate after Processing

Agglomerates comprising particles of abiraterone acetate having a particle size within the ranges specified herein, should be understood to fall within the scope of the present disclosure, regardless of whether the agglomerates exceed the ranges specified above.

Processing Time

In some embodiments, the abiraterone acetate and the grinding matrix are dry milled for the shortest time necessary to minimize any possible contamination from the mill process and/or any milling bodies utilized. This time varies greatly, depending on the abiraterone acetate and the grinding matrix, and may range from as short as 1 minute to several hours.

Suitable rates of agitation and total milling times are adjusted for the type and size of milling apparatus, the type and size of any milling media utilized, the weight ratio of the abiraterone acetate and grinding matrix mixture to the plurality of milling bodies that may be utilized, the chemical and physical properties of the abiraterone acetate and grinding matrix, and other parameters that may be optimized empirically.

In some embodiments, the grinding matrix (the materials milled together with abiraterone acetate) is not separated from the abiraterone acetate but is maintained with the abiraterone acetate in the final product. In some embodiments the grinding matrix is considered to be Generally Regarded as Safe (GRAS) for pharmaceutical products.

In an alternative aspect, the grinding matrix is separated from the abiraterone acetate. In one aspect, where the grinding matrix is not fully milled, the unmilled grinding matrix is separated from the abiraterone acetate. In a further aspect, at least a portion of the milled grinding matrix is separated from the abiraterone acetate.

Any portion of the grinding matrix may be removed, including but not limited to 10%, 25%, 50%, 75%, or substantially all of the grinding matrix.

In some embodiments of the disclosure, a significant portion of the milled grinding matrix may comprise particles of a size similar to and/or smaller than the particles comprising the abiraterone acetate. Where the portion of the milled grinding matrix to be separated from the particles comprising the abiraterone acetate comprises particles of a size similar to and/or smaller than the particles comprising the abiraterone acetate, separation techniques based on size distribution are inapplicable. In these circumstances, the method of the present disclosure may involve separation of at least a portion of the milled grinding matrix from the abiraterone acetate by techniques including, but not limited to, electrostatic separation, magnetic separation, centrifugation (density separation), hydrodynamic separation, and froth flotation. Advantageously, the step of removing at least a portion of the milled grinding matrix from the abiraterone acetate may be performed through means such as selective dissolution, washing, or sublimation.

In some cases grinding matrix that has two or more components where at least one component is water soluble and at least one component has low solubility in water can be used. In this case washing can be used to remove the matrix component soluble in water leaving the abiraterone acetate dispersed in the remaining matrix components. In a highly advantageous aspect of the disclosure the matrix with low solubility is a functional excipient.

In some cases the grinding matrix is appropriate for use in the method of the disclosure are also pharmaceutically acceptable and thus appropriate for use in a medicament. Where the method of the present disclosure does not involve complete separation of the grinding matrix from the abiraterone acetate, the present disclosure encompasses methods for the production of a medicament incorporating both the abiraterone acetate and at least a portion of the milled grinding matrix, medicaments so produced and methods of treatment of an animal, including man, using a therapeutically effective amount of said abiraterone acetate by way of said medicaments.

Abiraterone Acetate and Compositions

The present disclosure encompasses pharmaceutically acceptable materials produced according to the methods of the present disclosure, compositions including such materials, including compositions comprising such materials together with the grinding matrix with or without milling aids, facilitating agents, with at least a portion of the grinding matrix or separated from the grinding matrix.

Medicaments

The medicaments of the present disclosure may include the pharmaceutically acceptable material, optionally together with the grinding matrix or at least a portion of the grinding matrix, with or without milling aids, facilitating agents, combined with one or more pharmaceutically acceptable carriers, as well as other agents commonly used in the preparation of pharmaceutically acceptable compositions.

As used herein "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for parenteral administration, intravenous, intraperitoneal, intramuscular, sublingual, pulmonary, transdermal or oral administration. Pharmaceutically acceptable carriers include sterile aqueous solutions or dispersions and sterile powders for the extemporaneous preparation of sterile injectable solutions or dispersion. The use of such media and agents for the manufacture of medicaments is well known in the art. Except insofar as any conventional media or agent is incompatible with the pharmaceutically acceptable material, use thereof in the manufacture of a pharmaceutical composition according to the disclosure is contemplated.

Pharmaceutical acceptable carriers according to the disclosure may include one or more of the following examples:

(1) surfactants and polymers including, but not limited to polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, and their polymers, emulsifiers, sugar gum, starch, organic acids and their salts, vinyl pyrrolidone and vinyl acetate (2) binding agents such as various celluloses and cross-linked polyvinylpyrrolidone, microcrystalline cellulose; and or (3) filling agents such as lactose monohydrate, lactose anhydrous, microcrystalline cellulose and various starches; and or (4) lubricating agents such as agents that act on the flowability of the powder to be compressed, including colloidal silicon dioxide, talc, stearic acid, magnesium stearate, calcium stearate, silica gel; and or (5) sweeteners such as any natural or artificial sweetener including sucrose, xylitol, sodium saccharin, cyclamate, aspartame, and acesulfame K; and or (6) flavoring agents; and or (7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride; and or (8) buffers; and or (9) Diluents such as pharmaceutically acceptable inert fillers, such as microcrystalline cellulose, lactose, dibasic calcium phosphate, saccharides, and/or mixtures of any of the foregoing; and or

(10) wetting agents such as corn starch, potato starch, maize starch, and modified starches, and mixtures thereof; and or

(11) disintegrants; such as croscarmellose sodium, crospovidone, sodium starch glycolate, and or

(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and or

(13) other pharmaceutically acceptable excipients.

Actual dosage levels of abiraterone acetate disclosure may be varied in accordance with the nature of the abiraterone acetate, as well as the potential increased efficacy due to the advantages of providing and administering the abiraterone acetate (e.g., increased solubility, more rapid dissolution, increased surface area of the abiraterone acetate, etc.). Thus as used herein "therapeutically effective amount" will refer to an amount of abiraterone acetate required to effect a therapeutic response in an animal. Amounts effective for such a use will depend on: the desired therapeutic effect; the route of administration; the potency of the abiraterone acetate; the desired duration of treatment; the stage and severity of the disease being treated; the weight and general state of health of the patient; and the judgment of the prescribing physician.

Pharmacokinetic Properties of Abiraterone Acetate Compositions

Fast Onset of Absorbtion

In some embodiments, the abiraterone acetate compositions of the disclosure are rapidly absorbed. In one example, the abiraterone acetate compositions of the disclosure have a $T_{max}$, when administered to an adult male in the fasted state, of less than about 2.5 hours (about 3 hours to about 2 hours), less than about 2.0 hours, less than about 1.75 hours, less than about 1.5 hours, less than about 1.25 hours, and more than about 1.0 hour, for example between 1.5 and 2.0 hrs Increased Bioavailability The abiraterone acetate compositions of the disclosure exhibit increased bioavailability (AUC) and require smaller doses as compared to prior conventional compositions administered at the same dose (e.g., Zytiga®). In some cases an AUC and/or a Cmax similar to Zytiga® can be achieved at lower dose than for Zytiga®. Thus, in some cases the pharmaceutical compositions described herein administered at a lower dose than Zytiga provide comparable systemic exposure. For example, a 500 mg dose can be bioequivalent to a 1,000 mg dose of Zytiga®. Any drug composition can have adverse side effects. Thus, lower doses of drugs which can achieve the same or better therapeutic effect as those observed with larger doses of conventional compositions are desired. Such lower doses can be realized with the compositions of the disclosure because the greater bioavailability observed with the compositions as compared to conventional drug formulations means that smaller doses of drug are required to obtain the desired therapeutic effect.

The Pharmacokinetic Profiles of the Compositions of the Disclosure May be Less Affected by the Fed or Fasted State of the Subject Ingesting the Compositions The disclosure encompasses abiraterone acetate compositions wherein the pharmacokinetic profile of the composition is less affected by the fed or fasted state of a subject ingesting the composition compared to Zytiga®. This means that there is a less difference in the quantity of composition or the rate of composition absorption when the compositions are administered in the fed versus the fasted state. Thus, in some cases the compositions of the disclosure reduce the effect of food on the pharmacokinetics of the composition compared to Zytiga®.

The Pharmacokinetic Profiles of the Compositions of the Disclosure May Exhibit Reduced Inter-Patient Variability In some cases, the geometric mean coefficient of variation in one or more of Cmax, AUC0-t and AUC0-∞ may be less for an abiraterone acetate dosage form described herein than for Zytiga®. Thus, the geometric mean coefficient of variation in one or more of Cmax, AUC0-t and AUC0-∞ can be 10%-50% less (at least 10% less, 10%-30% less, or 10%-20% less) than for Zytiga®. (Calculated as CV (Zytiga®)-CV (present dosage form)/CV (Zytiga®)×100%).

Pharmacokinetic Protocol

Any standard pharmacokinetic protocol can be used to determine blood plasma concentration profile in humans following administration of a composition, and thereby establish whether that composition meets the pharmacokinetic criteria set out herein. For example, a randomized single-dose crossover study can be performed using a group of healthy adult human subjects. The number of subjects should be sufficient to provide adequate control of variation in a statistical analysis, and is typically about 10 or greater, although for certain purposes a smaller group can suffice. Each subject receives by oral administration at time zero a single dose (e.g., 100 mg) of a test formulation of composition, normally at around 8 am following an overnight fast. The subjects continue to fast and remain in an upright position for about 4 hours after administration of the composition. Blood samples are collected from each subject prior to administration (e.g., 15 minutes) and at several intervals after administration. For the present purpose it is to take several samples within the first hour, and to sample less frequently thereafter. Illustratively, blood samples could be collected at 15, 30, 45, 60, and 90 minutes after administration, then every hour from 2 to 10 hours after administration. Additional blood samples may also be taken later, for example at 12, 24, 36 and 48 hours after administration. If the same subjects are to be used for study of a second test formulation, a period of at least 7 days should elapse before administration of the second formulation. Plasma is separated from the blood samples by centrifugation and the separated plasma is analyzed for composition by a validated high performance liquid chromatography (HPLC) or liquid chromatography mass spectrometry (LCMS) procedure. Plasma concentrations of composition referenced herein are intended to mean total concentrations including both free and bound composition.

Modes of Administration of Medicaments Comprising Abiraterone Acetates

Medicaments of the disclosure can be administered to animals, including man, in any pharmaceutically acceptable manner, such as orally, rectally, pulmonary, intravaginally, locally (powders, ointments or drops), transdermal, parenteral administration, intravenous, intraperitoneal, intramuscular, sublingual or as a buccal or nasal spray.

Solid dosage forms for oral administration include capsules, tablets, pills, powders, pellets, and granules. Further, incorporating any of the normally employed excipients, such as those previously listed, and generally 5-95% of the biologically active agent, and more preferably at a concentration of 10%-75% will form a pharmaceutically acceptable non-toxic oral composition.

However, if the abiraterone acetate is to be utilized in a liquid suspension, the particles comprising the abiraterone acetate may require further stabilization once the solid carrier has been substantially removed to ensure the elimination, or at least minimization of particle agglomeration.

Example 1. Preparation of Fine Particle Abiraterone Acetate Powder Blend

Abiraterone acetate was dry milled in the presence of lactose monohydrate and sodium lauryl sulfate in the percentages shown in Table 1 to prepare a drug product intermediate for use in the preparation of tablets. Both lots of material were milled in a Union Process 1S attritor mill with a 0.5 gallon jacket-cooled tank. 200 g batches were milled with milling bodies for 40 minutes.

TABLE 1

Drug Product Intermediate for Preparation of Tablets

| Ingredient Name and Grade | Formula 1 % w/w | Formula 2 % w/w |
|---|---|---|
| Abiraterone Acetate | 20.00 | 30.00 |
| Lactose Monohydrate, USP | 78.50 | 67.75 |
| Sodium Lauryl Sulfate, NF | 1.50 | 2.25 |
| Total | 100.00 | 100.00 |

Example 2: Particle Size Analysis of Milled and Unmilled Abiraterone Acetate

The particle size distribution of the abiraterone acetate in the two drug product intermediate lots described in Example 1 were measured by light scattering using a Malvern Mastersizer 3000 model MAZ3000 particle size analyzer configured with a Hydro MV wet sample dispersion unit. Additionally, an unmilled blend of abiraterone acetate, lactose monohydrate and sodium lauryl sulfate was measured. All three samples were measured using the method as follows: the dispersant used was an aqueous solution of 0.1% povidone K30. Approximately 20 mg of sample powder and 5 mL of dispersant was added to a plastic centrifuge tube. The tube was swirled to disperse the powder and then sonicated (Branson Digital Sonifier 250 with sonic probe model 102C) for 1 minute at 20% amplitude with a sonication cycle of 5 seconds on and 15 seconds off. The particle size analyzer sample dispersion unit was filled with the dispersant and the sample was pipetted into the reservoir until the target obscuration of 5-15% was reached and remained constant. The stirrer was run at 1500 rpm, and data were collected for 10 seconds. Three measurements were made and the average values of each particle size parameter were reported. Table 2 and FIG. 1 show the particle size distributions; the data shows over a 10-fold reduction in particle size.

TABLE 2

Particle size Distribution of Unmilled and Milled Abiraterone Acetate

| | Unmilled | Formula 1 (20% AA) | Formula 2 (30% AA) |
|---|---|---|---|
| $D_{10}$ (micron) | 3.41 | 0.087 | 0.095 |
| $D_{50}$ (micron) | 8.50 | 0.199 | 0.225 |
| $D_{90}$ (micron) | 16.4 | 0.463 | 0.538 |
| $D_{4,3}$ (micron) | 9.32 | 0.254 | 0.280 |
| $D_{3,2}$ (micron) | 6.46 | 0.164 | 0.183 |

Example 3: Preparation of Tablets and Comparative Dissolution Studies

The milled drug product intermediate was combined with intragranular excipients and dry granulated using roller compaction and milling. The granulation was blended with extragranular excipients and compressed in a rotary tablet press to produce 100 mg abiraterone acetate tablets having the composition shown in Table 3.

TABLE 3

Abiraterone Acetate 100 mg Tablet Composition

| | Formula 1 | | Formula 2 | |
|---|---|---|---|---|
| Ingredient | % w/w | mg/tablet | % w/w | mg/tablet |
| Abiraterone Acetate DPI Formula 1 (20% AA) | 58.82 | 500.0 | | |
| Abiraterone Acetate DPI Formula 2 (30% AA) | | | 47.62 | 333.3 |
| Microcrystalline Cellulose, NF | 33.38 | 283.7 | 44.53 | 311.7 |
| Sodium Lauryl Sulfate, NF | 0.3 | 2.6 | 0.35 | 2.5 |
| Croscarmellose Sodium, NF | 7 | 59.5 | 7 | 49.0 |
| Sodium Stearyl Fumarate, NF | 0.5 | 4.3 | 0.5 | 3.5 |
| Total | 100 | 850.0 | 100 | 700.0 |

Figure 2:
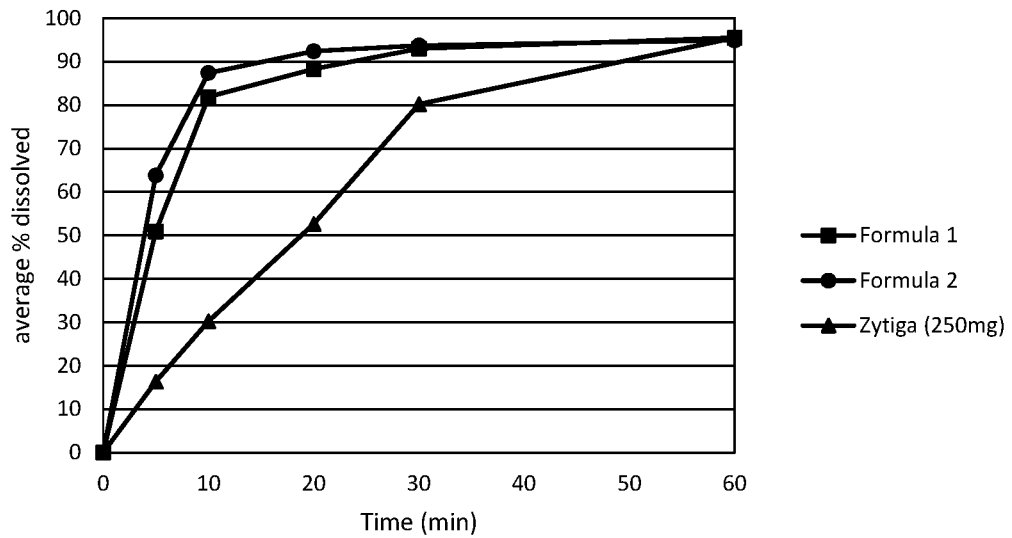
FIG. 2 is a graph of the results of dissolution rate measurements for abiraterone acetate tablets as described in Example 3.

The dissolution rates of the tablets prepared as described above were measured using the method listed on the FDA website for abiraterone acetate tablets, 250 mg; USP Apparatus II, 50 rpm in 900 mL of pH 4.5 buffer with 0.25% sodium lauryl sulfate. Samples were analyzed by UV at 270 nm. Additionally, for comparison purposes, Zytiga® tablets were tested with the same dissolution conditions. The results of this analysis are shown in Table 4 and FIG. 2. Full dissolution (>85% dissolved) was achieve in 10-20 minutes for the two tablet formulations contained milled abiraterone acetate, compared to Zytiga® which had full dissolution (>85% dissolved) in 60 minutes.

TABLE 4

Dissolution of Abiraterone Acetate Tablets

| | Formula 1 (100 mg abiraterone acetate) | | Formula 2 (100 mg abiraterone acetate) | | Zytiga ® (250 mg abiraterone acetate) | |
|---|---|---|---|---|---|---|
| Time [min] | Avg % dissolved | Std Deviation | Avg % dissolved | Std Deviation | % dissolved | Std Deviation |
| 0 | 0 | 0 | 0 | 0 | 0 | 0 |
| 5 | 50.9 | 14.3 | 63.8 | 12.4 | 16.3 | 1.8 |
| 10 | 81.9 | 10.9 | 87.4 | 6.4 | 30.2 | 2.8 |
| 20 | 88.3 | 2.9 | 92.4 | 4.8 | 52.6 | 3.3 |
| 30 | 93 | 9.1 | 93.7 | 4.8 | 80.2 | 9.7 |
| 60 | 95.5 | 7.1 | 94.9 | 4.4 | 95.5 | 1.2 |

Example 4: Abiraterone Acetate Tablets for Initial Phase I Study

Abiraterone acetate was dry milled in the presence of lactose monohydrate and sodium lauryl sulfate in the amounts shown in Table 5 to prepare a drug product intermediate for use in the preparation of tablets for use in Phase I testing. The material was milled in a Union Process 1S attritor mill with a 1.5 gallon jacket-cooled tank. The material was milled with milling bodies for 40 minutes.

TABLE 5

Drug Product Intermediate for Preparation of Tablets for Phase I Testing

| Ingredient Name and Grade | Weight percent | Quantity per batch (g) |
|---|---|---|
| Abiraterone Acetate | 30.00 | 300.0 |
| Lactose Monohydrate, USP | 67.75 | 677.5 |
| Sodium Lauryl Sulfate, NF | 2.25 | 22.5 |
| Total | 100.00 | 1000.0 |

The particle size distribution of the abiraterone acetate in the milled drug product intermediate was measured with a Micromeritics Saturn DigiSizer II 5205 particle size analyzer configured with an AquaPrep II sample cell. The instrument sample reservoir was filled with dispersant solution (0.1% povidone K30). The sample was prepared by adding 100 mg of milled powder and 20 mL of dispersant to a 30 mL glass bottle. The particles were dispersed by agitation with a pipette, and then the capped bottle was placed in an ultrasonic water bath (Branson Ultrasonic bath, Model 5510-MT, output 135 W, 42 KHz) such that the bath water level was half way up the side of the bottle. The sample was then sonicated for 30 minutes. The dispersed sample was added dropwise to the reservoir of the liquid sample handling unit until an obscuration value of approximately 7% was reached. The internal sonic probe was run at 100% intensity for 300 seconds, and then the sample was circulated for 120 seconds before data collection. Data were collected at a beam angle setting of 65° when the obscuration value was between 5 and 10%. Each measurement was repeated in triplicate and the average of three measurements was reported. Particle size data from the milled powder are reported in Table 6.

TABLE 6

Milled Abiraterone Acetate Particle Size

| Particle Size Parameter | Result (micron) |
|---|---|
| $D_{10}$ | 0.105 |
| $D_{50}$ | 0.387 |
| $D_{90}$ | 1.308 |
| $D_{4,3}$ | 0.588 |
| $D_{3,2}$ | 0.247 |

The milled drug product intermediate was combined with intragranular excipients and dry granulated using roller compaction and milling. The granulation was blended with extragranular excipients and compressed in a rotary tablet press to produce 100 mg abiraterone acetate tablets having the composition shown in Table 7.

TABLE 7

Abiraterone Acetate 100 mg Tablet Composition for Initial Phase 1 Testing

| Ingredient | % w/w | mg/tablet |
|---|---|---|
| Abiraterone Acetate | 14.29 | 100.0 |
| Lactose Monohydrate, NF | 32.26 | 225.8 |
| Sodium Lauryl Sulfate, NF | 1.42 | 10.0 |
| Microcrystalline Cellulose, NF | 44.53 | 311.7 |
| Croscarmellose Sodium, NF | 7.00 | 49.0 |
| Sodium Stearyl Fumarate, NF | 0.50 | 3.5 |
| Total | 100.00 | 700.0 |

The dissolution rates of the tablets prepared as described above were measured in USP Apparatus II, 75 rpm in 900 mL of pH 4.5 buffer with 0.1% SLS. Samples were analyzed by HPLC. Additionally, for comparison purposes, Zytiga® tablets were tested with the same dissolution conditions. Because Zytiga® tablets are 250 mg which is approaching the solubility limit of the dissolution media, the tablets were cut to a weight equivalent to 100 mg of abiraterone acetate. Zytiga® samples were measured using UV at 270 nm. The results of this analysis are shown in Table 8; full dissolution (>85% dissolved) of the prepared tablets was achieved in 5 minutes, whereas the Zytiga® tablets dissolution was achieved in 20 minutes.

TABLE 8

Dissolution of Abiraterone Acetate Tablets 100 mg

| | 100 mg Tablets for Phase 1 Clinical testing | | Zytiga ® tablets (cut to 100 mg) | |
|---|---|---|---|---|
| Time (minutes) | Average % dissolved | % RSD | Average % dissolved | % RSD |
| 5 | 88 | 7.2 | 32.7 | 27.1 |
| 10 | 99 | 1.8 | 59.0 | 21.3 |
| 15 | 99 | 1.1 | 78.2 | 9.6 |
| 20 | — | — | 91.6 | 6.7 |
| 30 | 100 | 1.1 | 97.1 | 4.0 |
| 45 | 100 | 1.2 | 97.6 | 3.8 |
| 60 | 100 | 1.2 | 97.7 | 3.8 |

Example 5: Phase I Study of 100, 200, and 400 mg Doses of Abiraterone Acetate Formulation Compared to Zytiga® 1000 mg The abiraterone acetate 100 mg tablet formulation prepared as described in Example 4 was tested in healthy male patients under fasting conditions at 100 mg, 200 mg, and 400 mg doses (1, 2, or 4×100 mg tablets respectively). In the same study, a 1000 mg dose of Zytiga® was tested (4×250 mg tablets). The results of this study are shown in Table 9.

TABLE 9

Abiraterone Acetate Tablets 100 mg Pharmacokinetic Data (Arithmetic Means)

| | | Milled Abiraterone Acetate | | | Zytiga ® |
|---|---|---|---|---|---|
| PK Parameters | Statistics | 100 mg | 200 mg | 400 mg | 1,000 mg |
| $AUC_{0\text{-}inf}$ (ng · hr/mL) | N | 19 | 18 | 19 | 19 |
| | Mean* | 74.49 | 183.34 | 319.92 | 421.23 |
| | S.D. | 42.22 | 86.7 | 140.74 | 183.83 |
| | CV (%) | 56.68 | 47.29 | 43.99 | 43.64 |
| $AUC_{0\text{-}t}$ (ng · hr/mL) | N | 19 | 18 | 19 | 19 |
| | Mean* | 67.55 | 169.99 | 302.9 | 387.34 |
| | S.D. | 39.37 | 83.73 | 137.17 | 168.67 |
| | CV (%) | 58.28 | 49.25 | 45.29 | 43.55 |
| $C_{max}$ (ng/mL) | N | 19 | 18 | 19 | 19 |
| | Mean* | 17.28 | 39.11 | 65.42 | 79.46 |
| | S.D. | 10.41 | 21.69 | 35.58 | 39.56 |
| | CV (%) | 60.29 | 55.46 | 54.39 | 49.78 |
| $T_{max}$ (hour) | N | 19 | 18 | 19 | 19 |
| | Mean | 1.55 | 1.78 | 2.32 | 2.16 |
| | S.D. | 0.57 | 0.77 | 1.33 | 0.78 |
| | CV (%) | 37.02 | 43.38 | 57.22 | 36.27 |
| $t_{1/2}$ (hr) | N | 19 | 18 | 19 | 19 |
| | Mean* | 4.72 | 7.83 | 8.84 | 14.48 |
| | S.D. | 2.57 | 3.88 | 2.96 | 5.11 |
| | CV (%) | 54.35 | 49.51 | 33.45 | 35.32 |

TABLE 9-continued

Abiraterone Acetate Tablets 100 mg Pharmacokinetic Data (Arithmetic Means)

| PK Parameters | Statistics | Milled Abiraterone Acetate | | | Zytiga ® |
|---|---|---|---|---|---|
| | | 100 mg | 200 mg | 400 mg | 1,000 mg |
| Ke (hr$^{-1}$) | N | 19 | 18 | 19 | 19 |
| | Mean | 0.18 | 0.11 | 0.09 | 0.05 |
| | S.D. | 0.08 | 0.05 | 0.03 | 0.02 |
| | CV (%) | 43.38 | 45.27 | 30.8 | 36.98 |

*Observed differences were highly significant ($p < 0.0001$, ANOVA) among the four treatments.
^Observed differences were significant ($p < 0.05$, Wilcoxon signed rank test), compared to Zytiga ® 1,000 mg.

Example 6: Stability of Abiraterone Acetate Powder Blends and Tablets

Figure 3A:
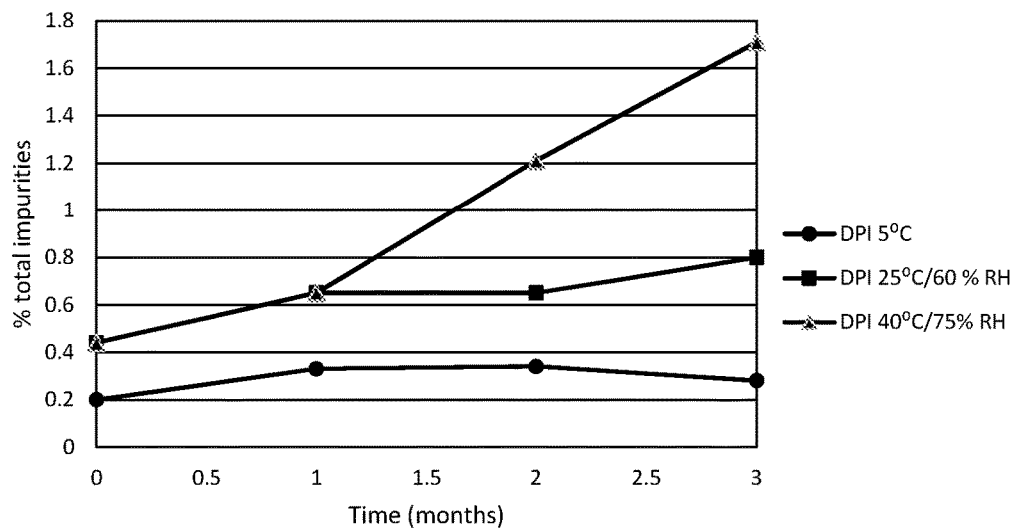
FIGS. 3A and 3B are graphs depicting the results of stability studies described in Example 6.
Figure 3B:
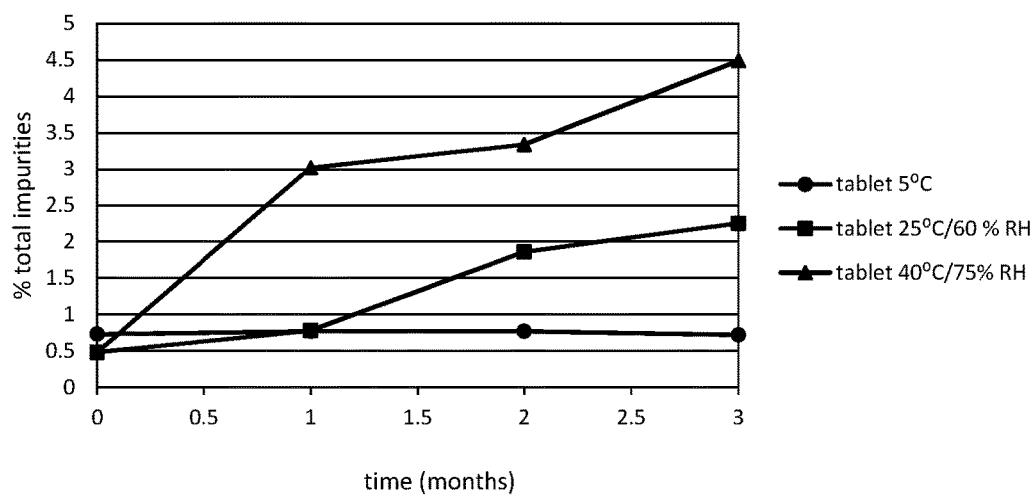

Total impurity growth of 0.2-0.6% AUC was detected by HPLC after abiraterone acetate was dry milled with lactose monohydrate and sodium lauryl sulfate. When the milled abiraterone acetate powder blend (or drug product intermediate; "DPI") was further processed into tablets, the level of impurities was found to be higher, about 0.5-1.1%. Stability testing showed that the impurities grew at 25° C./60% RH and at 40° C./75% RH, but did not grow at 2-8° C. In addition, impurity growth in the tablets was faster than that in the milled DPI. Table 10 and FIGS. 3A and 3B (diamonds, 5° C.; squares, 25° C./60% RH; and triangles, 40° C./75% RH) provide an overview of the impurity levels in lots of milled DPI and tablets upon accelerated stability testing. Tablets stored refrigerated had an acceptably low level of impurities, but it is desirable to have formulation that can be stored under ambient conditions.

TABLE 10

Abiraterone Acetate Stability (total impurities)

| Time (months) | Abiraterone Acetate DPI (contains milled API) | | | Abiraterone Acetate tablets, 100 mg (contains milled API) | | |
|---|---|---|---|---|---|---|
| | 5° C. | 25° C./ 60% RH | 40° C./ 75% RH | 5° C. | 25° C./ 60% RH | 40° C./ 75% RH |
| 0 | 0.20 | 0.44 | 0.44 | 0.73 | 0.48 | 0.48 |
| 1 | 0.33 | 0.65 | 0.65 | 0.77 | 0.78 | 3.02 |
| 2 | 0.34 | 0.65 | 1.21 | 0.77 | 1.86 | 3.34 |
| 3 | 0.28 | 0.8 | 1.71 | 0.72 | 2.25 | 4.49 |

The impurity growth in the DPI and tablets containing fine particle abiraterone acetate is due to oxidative degradation of abiraterone acetate. Aged Zytiga® (abiraterone acetate) tablets were tested for purity, and the impurity levels were found to be much lower than aged tablets containing fine particle abiraterone acetate. The faster degradation in tablets containing fine particle abiraterone acetate could arise from a number of sources, including, but not limited to: greater surface area of the API, higher proportion of excipient relative to the API, and differences in excipients. Further studies found that the API has some degradation in the presence of the excipients, but the degradation is greatly accelerated once the mixture is milled. Data are provided in Table 11.

TABLE 11

Abiraterone Acetate Stability

| Product | Milling | Stability | Total impurities by HPLC (% AUC) |
|---|---|---|---|
| Abiraterone Acetate (API) | none | 80° C., 4 hrs | 0.23 |
| | SPEX shaker mill | 80° C., 4 hrs | 0.17 |
| Drug Product Intermediate (API, SLS, lactose monohydrate) | none | 80° C., 4 hrs | 0.28 |
| | SPEX shaker mill | 80° C., 4 hrs | 3.90 |
| Tablet formulation (API, SLS, lactose monohydrate, microcrystalline cellulose, croscarmellose sodium, sodium stearyl fumarate) | none | 80° C., 4 hrs | 0.76 |
| | SPEX shaker mill | 105° C., 4 hrs | 10.00 |
| Zytiga ® (abiraterone acetate) tablet | None | Stored room temperature until expiry | 0.20 |

Example 7: Milling of Abiraterone with Antioxidant or Sequestering Agent

Dry milling of abiraterone acetate was carried out in the presence of lactose monohydrate and sodium lauryl sulfate and various antioxidants and/or sequestering agents. In one study the dry milling included a combination of ascorbic acid and fumaric acid or a combination of butylated hydroxyanisole (BHA) and butylated hydroxytoluene (BHT): the formulations are shown in Table 12. Each lot was milled in a Union Process 1S attritor mill with a 0.5 gallon jacket-cooled tank. 200 g batches were milled with milling bodies for 40 minutes. Both DPI Formulas contained abiraterone acetate having a $D_{90}$ below 1,000 nm, when tested per the light scattering method described in Example 2.

TABLE 12

DPI Formulation Containing Antioxidant or Sequestering Agent

| Ingredient | Function | DPI Formulation Ascorbic/ Fumaric % w/w | DPI Formulation BHA/BHT % w/w |
|---|---|---|---|
| Abiraterone Acetate | Active | 30.00 | 30.00 |
| Lactose Monohydrate | Grinding compound | 67.35 | 67.65 |
| Sodium lauryl sulfate | Facilitating agent | 2.25 | 2.25 |
| Ascorbic acid | Antioxidant | 0.20 | |
| Fumaric acid | Sequestering agent | 0.20 | |
| Butylated Hydroxyanisole (BHA) | Antioxidant | | 0.05 |
| Butylated Hydroxytoluene (BHT) | Antioxidant | | 0.05 |
| TOTAL | | 100.00 | 100.00 |

The two different DPI Formulations were used to prepare two different corresponding tablet Formulation as detailed in Table 13 by adding the indicated excipients to the DPI Formulations, dry granulating and tableting.

TABLE 13

Tablet Formulations Containing Antioxidant or Sequestering Agent

| | Function | Tablet Formulation Ascorbic/ Fumaric % w/w | Tablet Formulation BHA/BHT % w/w |
|---|---|---|---|
| DPI Formulation Ascorbic/ Fumaric (abiraterone acetate, lactose monohydrate, SLS, ascorbic acid, fumaric acid) | | 47.62 | |
| DPI Formulation BHA/BHT (abiraterone acetate, lactose monohydrate, SLS, BHA, BHT) | | | 47.62 |
| Microcrystalline cellulose | Diluent | 44.53 | 44.53 |
| Sodium lauryl sulfate | Wetting agent | 0.35 | 0.35 |
| Croscarmellose sodium | Disintegrant | 7.0 | 7.0 |
| Sodium stearyl fumarate | Lubricant | 0.5 | 0.5 |
| Total | | 100 | 100 |

The stability of the two tablet formulations was tested under accelerated conditions. Table 14 contains data demonstrating that both tablet formulations with antioxidant had dramatically improved stability after 3 months storage at 40° C./75% RH compared to the formulation without antioxidant, with the BHA/BHT formulation nearly halting all degradation. This demonstrates that the addition of antioxidants and/or sequestering agents during milling can dramatically improve stability.

TABLE 14

Tablet Stability data with and without Antioxidant

| | No antioxidant | | Formulation Ascorbic Acid and Fumaric Acid | | Formulation BHA&BHT | |
|---|---|---|---|---|---|---|
| condition | Assay (% label claim) | Total impurities (% AUC) | Assay (% label claim) | Total Impurities (% AUC) | Assay (% label claim) | Total Impurities (% AUC) |
| Initial | 98.6 | 0.48 | 101.5 | 0.31 | 101.6 | 0.16 |
| 1 month, 25° C./60% RH | 98.1 | 0.78 | 100.9 | 0.89 | 101.1 | 0.15 |
| 1 month, 40° C./75% RH | 92.4 | 3.02 | 96.8 | 1.13 | 100.7 | 0.19 |
| 2 month, 25° C./60% RH | 97.5 | 1.86 | 95.5 | 1.26 | 96.7 | 0.13 |
| 2 month, 40° C./75% RH | 92.8 | 3.36 | 97.5 | 1.46 | 97.4 | 0.16 |
| 3 months, 25° C./60% RH | 95.2 | 2.25 | 97.8 | 1.75 | 95.5 | 0.45 |
| 3 months, 40° C./75% RH | 92.5 | 4.49 | 96.0 | 1.90 | 98.6 | 0.70 |

The dissolution rate of the abiraterone acetate in the Tablet Formulation Ascorbic/Fumaric and Tablet Formulation BHA/BHT was tested using USP Apparatus II at 75 rpm in 900 ml of pH 4.5 phosphate buffer with 0.1% SLS. Tablets for all three types of tablets had full dissolution (>85% of the abiraterone acetate dissolved) within 10 minutes.

Example 8: Abiraterone Acetate Tablets for Additional Phase I Studies

An additional drug product intermediate formulation was prepared by dry milling abiraterone acetate, lactose monohydrate, sodium lauryl sulfate, BHA and BHT. The composition of the material milled to form this intermediate is shown in Table 15. The formulation was milled in a custom jacket-cooled 62 gallon attritor mill; the powder blend was milled with milling bodies for 72 minutes.

TABLE 15

Milled Drug Product Intermediate Containing BHA and BHT for Phase 1 clinical studies

| Component | Weight percent | Quantity per batch (g) |
|---|---|---|
| Abiraterone Acetate | 30.0 | 8.400 |
| Lactose Monohydrate, USP | 63.8 | 17.886 |
| Sodium Lauryl Sulfate, NF | 6.0 | 1.680 |
| BHA | 0.1 | 0.028 |
| BHT | 0.1 | 0.028 |
| Total | 100 | 28.000 |

The particle size distribution of the abiraterone acetate in this drug product intermediate was measured by light scattering using a Malvern Mastersizer 3000 model MAZ3000 particle size analyzer configured with a Hydro MV wet sample dispersion unit. Two different methods were used to measure the particle size distributions, as described below:

Method 1: The dispersant used was an aqueous solution of 0.1% povidone K30. Approximately 20 mg of sample powder and 5 mL of dispersant was added to a plastic centrifuge tube. The tube was swirled to disperse the powder and then sonicated (Branson Digital Sonifier 250 with sonic probe model 102C) for 1 minute at 20% amplitude with a sonication cycle of 5 seconds on and 15 seconds off. The particle size analyzer sample dispersion unit was filled with the dispersant and the sample was pipetted into the reservoir until the target obscuration of 5-15% was reached and remained constant. The stirrer was run at 1500 rpm, and data were collected for 10 seconds. Three measurements were made and the average values of each particle size parameter were reported.

Method 2: The dispersant used was an aqueous solution comprising 0.1% of poloxamer 338 and 0.1% calcium chloride which was filtered through a 0.2 μm nylon filter prior to use. Approximately 20 mg of sample powder and 5 mL of dispersant solution was added to a glass vial. The vial was capped and swirled to disperse the powder particles. The vial cap was then loosened and the vial placed in the center of a sonic bath (Elma Elmsonic P30H ultrasonic bath). The vial was immersed such that the bath liquid level was above the level of the dispersant in the vial, but the vial was not touching the bottom of the bath. The sample was sonicated at 37 kHz at 100% power for ten minutes. The particle size analyzer sample dispersion unit was filled with dispersant and the sample was pipetted into the reservoir until an obscuration of 5-15% was obtained and remained constant. The stirrer was run at 1500 rpm, and data were collected for 10 seconds. Three measurements were made and the average values of each particle size parameter were reported.

Table 16 presents a comparison of the particle size values for abiraterone acetate in the drug product intermediate (DPI) described in Table 15 before and after milling, using Methods 1 and 2 described above.

TABLE 16

Particle Size Distribution Data for Abiraterone Acetate DPI Containing BHA and BHT

| | Particle Size (μm) | | |
|---|---|---|---|
| Parameter | Unmilled Method 1 | Milled Method 1 | Milled Method 2 |
| $D_{10}$ | 1.64 | 0.153 | 0.124 |
| $D_{50}$ | 3.07 | 0.747 | 0.286 |
| $D_{90}$ | 5.79 | 3.250 | 0.937 |
| $D_{4,3}$ | 3.44 | 1.300 | 0.479 |
| $D_{3,2}$ | 2.75 | 0.390 | 0.241 |

The milled drug product intermediate was combined with intragranular excipients and dry granulated using roller compaction and milling. The granulation was blended with extragranular excipients and compressed in a rotary tablet press to produce 125 mg abiraterone acetate tablets having the composition shown in Table 17.

TABLE 17

Milled Abiraterone Acetate Tablets 125 mg Composition

| Component | % w/w | mg/tablet |
|---|---|---|
| Abiraterone Acetate | 14.37 | 125.00 |
| Lactose Monhydrate, NF | 30.56 | 265.83 |
| Sodium Lauryl Sulfate, NF | 2.87 | 25.00 |
| BHA (butylated hydroxyanisole), NF | 0.05 | 0.42 |
| BHT (butylated hydroxytoluene), NF | 0.05 | 0.42 |
| Microcrystalline Cellulose, NF | 44.60 | 388.06 |
| Croscarmellose Sodium, NF | 7.00 | 60.90 |
| Sodium Stearyl Fumarate, NF | 0.50 | 4.38 |
| Total | 100.00 | 870.00 |

The dissolution rate of these tablets was measured in at USP Apparatus II, 75 rpm in pH 4.5 buffer with 0.12% SLS. Samples were analyzed by HPLC. The results of this analysis are shown in Table 18; full dissolution (>85% dissolved) was achieved in 10 minutes.

TABLE 18

Dissolution of Abiraterone Acetate Tablets

| Time (minutes) | % abiraterone acetate dissolved | % RSD |
|---|---|---|
| 5 | 53 | 6.6 |
| 10 | 86 | 3.4 |
| 15 | 93 | 3.5 |
| 30 | 95 | 2.9 |
| 45 | 95 | 3.1 |
| 60 | 95 | 3.0 |

Example 11: Phase I Study of 125, 500, and 625 mg Doses of Abiraterone Acetate Formulation Compared to Zytiga 1000 mg The abiraterone acetate 125 mg tablet formulation prepared as described in Example 10 was tested in healthy male patients under fasting conditions at 125 mg, 500 mg, and 625 mg doses (1, 4, or 5×125 mg tablets respectively). In the same study, a 1000 mg dose of Zytiga® was tested (4×250 mg tablets). The results of this study are shown in Table 19.

TABLE 19

Abiraterone Acetate Tablets 125 mg
Pharmacokinetic Data (Arithmetic Means)

| | | Milled Abiraterone Acetate | | | Zytiga ® |
|---|---|---|---|---|---|
| PK Parameters | Statistics | 125 mg | 500 mg | 625 mg | 1,000 mg |
| $AUC_{0-inf}$ (ng · hr/mL) | N | 33 | 34 | 34 | 33 |
| | Mean* | 112.12 | 438.02 | 473.31 | 453.18 |
| | S.D. | 65.94 | 249.43 | 247.19 | 219.07 |
| | CV (%) | 58.81 | 56.94 | 52.23 | 48.34 |
| $AUC_{0-t}$ (ng · hr/mL) | N | 33 | 34 | 34 | 34 |
| | Mean* | 102.55 | 416.23 | 450.19 | 415.91 |
| | S.D. | 63.27 | 245.73 | 241.85 | 210.67 |
| | CV (%) | 61.7 | 59.04 | 53.72 | 50.65 |
| $C_{max}$ (ng/mL) | N | 33 | 34 | 34 | 34 |
| | Mean* | 28.22 | 84.16 | 100.76 | 83.4 |
| | S.D. | 16.46 | 44.05 | 63.75 | 57.4 |
| | CV (%) | 58.34 | 52.34 | 63.27 | 68.83 |
| $T_{max}$ (hour) | N | 33 | 34 | 34 | 34 |
| | Mean | 1.61 | 1.79 | 1.84 | 2.21 |
| | S.D. | 0.98 | 1.12 | 0.97 | 1.44 |
| | CV (%) | 61.16 | 62.55 | 52.61 | 65.34 |
| $t_{1/2}$ (hr) | N | 33 | 34 | 34 | 33 |
| | Mean* | 7.2 | 14.2 | 14.54 | 20.64 |
| | S.D. | 3.47 | 6.44 | 5.54 | 9.03 |
| | CV (%) | 48.28 | 45.61 | 38.07 | 43.75 |
| Ke (/hr) | N | 33 | 34 | 34 | 33 |
| | Mean | 0.13 | 0.06 | 0.05 | 0.04 |
| | S.D. | 0.09 | 0.05 | 0.02 | 0.02 |
| | CV (%) | 65.7 | 71.26 | 36.1 | 46.69 |

Example 12: Additional Abiraterone Acetate Powder and Tablets

An additional drug product intermediate formulation was prepared by dry milling abiraterone acetate, lactose monohydrate, sodium lauryl sulfate, BHA and BHT. The composition of the material milled to form this intermediate is shown in Table 16. Two batches were milled with varying processing conditions, yielding slightly different particle size.

TABLE 16

Additional Milled Drug Product Intermediate

| Ingredient | Weight percent | Quantity per batch (g) |
|---|---|---|
| Abiraterone Acetate | 30.00 | 450.00 |
| Lactose Monohydrate, USP | 67.55 | 1013.25 |
| Sodium Lauryl Sulfate, NF | 2.25 | 33.75 |
| Butylated Hydroxytoluene (BHT) | 0.10 | 1.50 |
| Butylated Hydroxyanisole (BHA) | 0.10 | 1.50 |
| total | 100.00 | 1500.0 |

The particle size distribution of the abiraterone acetate in both lots of drug product intermediate were measured by light scattering using a Malvern Mastersizer 3000 model MAZ3000 particle size analyzer configured with a Hydro MV wet sample dispersion unit. Method 1 described in example 8 was utilized to obtain the particle size distribution shown in Table 17.

TABLE 17

Additional Particle Size Distribution Data for Abiraterone Acetate DPI

| | Particle Size (μm) | | |
|---|---|---|---|
| Parameter | Unmilled | Batch 1, Milled | Batch 2, Milled |
| $D_{10}$ | 1.69 | 1.17 | 1.36 |
| $D_{50}$ | 3.55 | 2.13 | 2.46 |
| $D_{90}$ | 7.58 | 4.17 | 4.64 |
| $D_{4,3}$ | 5.94 | 5.45 | 4.46 |
| $D_{3,2}$ | 3.02 | 1.95 | 2.25 |

The milled drug product intermediate from Batch 1 was combined with intragranular excipients and dry granulated using roller compaction and milling. The granulation was blended with extragranular excipients and compressed in a rotary tablet press to produce 100 mg abiraterone acetate tablets having the composition shown in Table 18.

TABLE 18

Milled Abiraterone Acetate Tablets 100 mg Composition

| Component | % w/w | mg/tablet |
|---|---|---|
| Abiraterone Acetate | 14.29 | 100.0 |
| Lactose Monhydrate, NF | 32.17 | 10.0 |
| Sodium Lauryl Sulfate, NF | 1.42 | 0.3 |
| BHA (butylated hydroxyanisole), NF | 0.05 | 0.3 |
| BHT (butylated hydroxytoluene), NF | 0.05 | 225.2 |
| Microcrystalline Cellulose, NF | 44.53 | 311.7 |
| Croscarmellose Sodium, NF | 7.00 | 49.0 |
| Sodium Stearyl Fumarate, NF | 0.50 | 3.5 |
| Total | 100.0 | 700.0 |

The dissolution rate of these tablets was measured in at USP Apparatus II, 75 rpm in pH 4.5 buffer with 0.1% SLS. Samples were analyzed by UV at 270 nm. The results of this analysis are shown in Table 19; full dissolution (>85% dissolved) was achieved in 10 minutes.

TABLE 19

Dissolution of Abiraterone Acetate Tablets, 100 mg

| Time (minutes) | % abiraterone acetate dissolved | % RSD |
|---|---|---|
| 5 | 60.2 | 7.1 |
| 10 | 94.3 | 4.0 |
| 15 | 97.6 | 3.4 |
| 30 | 98.8 | 2.1 |
| 45 | 98.2 | 2.3 |
| 60 | 98.3 | 2.3 |

Example 13: Stability of Tablets

An additional drug product intermediate formulation was prepared by dry milling abiraterone acetate, lactose monohydrate, sodium lauryl sulfate, BHA and BHT. The composition of the material milled to form this intermediate is shown in Table 20.

TABLE 20

Milled Drug Product Intermediate Containing BHA and BHT

| Ingredient | Weight percent | Quantity per batch (kg) |
|---|---|---|
| Abiraterone Acetate | 30.00 | 7.44 |
| Lactose Monohydrate, USP | 63.8 | 15.82 |
| Sodium Lauryl Sulfate, NF | 6.0 | 1.49 |
| Butylated Hydroxytoluene (BHT) | 0.10 | 0.025 |
| Butylated Hydroxyanisole (BHA) | 0.10 | 0.025 |
| total | 100.00 | 24.80 |

The particle size distribution of the abiraterone acetate in this drug product intermediate was measured by light scattering using a Malvern Mastersizer 3000 model MAZ3000 particle size analyzer configured with a Hydro MV wet sample dispersion unit. Method 1 described in example 8 was utilized to obtain the particle size distribution shown in Table 21.

TABLE 21

Additional Particle Size Distribution Data for Abiraterone Acetate DPI Containing BHA and BHT

| | Particle Size (μm) | |
|---|---|---|
| Parameter | Unmilled | Milled |
| $D_{10}$ | 1.69 | 0.184 |
| $D_{50}$ | 3.55 | 1.20 |
| $D_{90}$ | 7.58 | 3.57 |
| $D_{4,3}$ | 5.94 | 1.56 |
| $D_{3,2}$ | 3.02 | 0.49 |

The milled drug product intermediate was combined with intragranular excipients and dry granulated using roller compaction and milling. The granulation was blended with extragranular excipients and compressed in a rotary tablet press to produce 125 mg abiraterone acetate tablets having the composition shown in Table 22.

TABLE 22

Milled Abiraterone Acetate Tablets 125 mg Composition

| Ingredient | % w/w | mg/tablet |
|---|---|---|
| Abiraterone acetate | 14.34 | 125.00 |
| Lactose monohydrate, USP | 30.49 | 265.83 |
| Butylated Hydroxytoluene (BHT) | 0.05 | 0.42 |
| Butylated Hydroxyanisole (BHA) | 0.05 | 0.42 |
| sodium lauryl sulfate, NF | 2.87 | 25.00 |
| Microcrystalline cellulose, NF | 44.69 | 389.63 |
| Croscarmellose sodium, NF | 7.02 | 61.25 |
| Sodium stearyl fumarate, NF | 0.50 | 4.38 |
| total | 100.00 | 871.92 |

Tablets were packaged and mounted on accelerated stability at 40° C. and 75% relative humidity. Impurities were measured by a stability-indicating HPLC method. The dissolution rate of these tablets was measured in at USP Apparatus II, 75 rpm in pH 4.5 buffer with 0.12% SLS. The results are shown in Table 23; no impurity growth was observed over 3 months at 40° C./75% RH, and the dissolution remained unchanged with full dissolution (>85% dissolved) within 10 minutes over 3 months at 40° C./75% RH.

TABLE 23

Stability of Abiraterone Acetate Tablets, 125 mg
Abiraterone Acetate Tablets, 125 mg

| | Initial | | 1 month 40° C./75% RH | | 2 month 40° C./75% RH | | 3 month 40° C./75% RH | |
|---|---|---|---|---|---|---|---|---|
| Total Impurities (% AUC) | | | | | | | | |
| | 0.05 | | <0.05 | | 0.05 | | <0.05 | |
| Time (minutes) | Avg % dissolved (n = 6) | % RSD | Avg % dissolved (n = 3) | % RSD | Avg % dissolved (n = 3) | % RSD | Avg % dissolved (n = 3) | % RSD |
| 4 | 60.8 | 10.2 | 60.3 | 8.3 | 63.4 | 8.0 | 65.3 | 8.6 |
| 6 | 81.3 | 8.3 | 80.0 | 5.0 | 87.2 | 3.0 | 85.8 | 2.9 |
| 8 | 92.1 | 1.5 | 91.6 | 4.2 | 94.2 | 1.2 | 93.8 | 0.7 |
| 10 | 93.9 | 1.2 | 93.6 | 2.9 | 95.5 | 0.8 | 95.3 | 0.6 |
| 20 | 95.0 | 1.4 | 97.4 | 1.9 | 97.4 | 0.6 | 97.4 | 0.4 |
| 30 | 95.3 | 1.4 | 97.7 | 0.6 | 98.0 | 0.3 | 97.3 | 0.8 |
| 40 | 95.4 | 1.9 | 98.0 | 0.1 | 99.3 | 2.9 | 97.0 | 1.2 |
| 60 | 98.1 | 4.7 | 97.4 | 0.7 | 99.0 | 1.2 | 97.2 | 0.7 |

Example 14: Effect of Fed or Fasted State

The effect of a high fat meal on the oral bioavailability of a 500 mg dose of 125 mg milled abiraterone mg tablets was evaluated in a single-center, single-dose, randomized, open-label, 2-period, 2-treatment crossover pharmacokinetic study. During the first dosing period, approximately half of the subjects were administered the test article with 240 mL of water, after a 10 hour fast. The remaining subjects were given the test article approximately 30 minutes after consuming a standard FDA high fat breakfast. After a seven day washout period, each subject was crossed over to the other treatment. Plasma samples were taken immediately prior to dosing and at 0.25, 0.5, 1.0, 1.5, 2.0, 3.0, 4.0, 6.0, 8.0, 12.0, 18.0, 24.0, and 48.0 hours after administration of the test article. Samples were analyzed for abiraterone concentration, and the results were used to calculate pharmacokinetic parameters ($AUC_{0-\infty}$, $AUC_{0-t}$, and $C_{max}$) for each subject and treatment. The geometric mean values for $AUC_{0-\infty}$, $AUC_{0-t}$, and $C_{max}$ when the test article was administered in the fed state were 1444.1 ng·h/mL, 1393.4 ng·h/mL, and 443.7 ng/mL respectively, while the geometric mean values for those same parameters were 322.7 ng·h/mL, 301.0 ng·h/mL, and 67.9 ng/mL when the drug was administered in the fasted state. The ratios (fed/fasted) for $AUC_{0-\infty}$, $AUC_{0-t}$, and $C_{max}$ were 4.48, 4.63, and 6.53, respectively.

The invention claimed is:

1. A solid oral unit dosage form of abiraterone acetate containing 125 mg of abiraterone acetate having a [D50] greater than 100 nm and less than 1200 nm, the unit dosage form further comprising lactose monohydrate, sodium lauryl sulfate, microcrystalline cellulose, croscarmellose sodium, sodium stearyl fumarate, butylated hydroxyanisole, and butylated hydroxytoluene,
   wherein a 500 mg dose of the unit dosage form is bioequivalent to a 1000 mg dose of Zytiga® Tablets (250 mg; National Drug Code Number 57894-150; NDA 202379) in healthy male subjects in the fasted state;
   wherein the dissolution rate of the abiraterone acetate in the unit dosage form is such that when the unit dosage form is tested in 900 ml of pH 4.5 phosphate buffer with 0.12% sodium lauryl sulfate using USP Apparatus II at 75 rpm, at least 70% of the abiraterone acetate dissolves in between 5 and 15 minutes; and
   wherein a 500 mg dose, upon oral administration to a population of healthy male subjects in the fasted state, provides a mean blood plasma $C_{max}$ of 50-120 ng/ml and a mean blood plasma $AUC_{(0-\infty)}$ of 240-650 h×ng/ml.

2. The unit dosage form of abiraterone acetate of claim 1, wherein the ratio of the log of the geometric mean of the $AUC_{(0-\infty)}$ for a 500 mg dose administered to healthy male subjects in the fasted state compared to a 1000 mg dose of Zytiga® Tablets (250 mg; National Drug Code Number 57894-150; NDA 202379) administered to healthy male subjects in the fasted state is selected from: 0.6 to 1.4, 0.7 to 1.3, 0.8 to 1.2 and 0.9 to 1.1.

3. The unit dosage form of abiraterone acetate of claim 1, wherein the ratio of the log of the geometric mean of the $C_{max}$ for a 500 mg dose administered to healthy male subjects in the fasted state compared to a 1000 mg dose of Zytiga® Tablets (250 mg; National Drug Code Number 57894-150; NDA 202379) administered to healthy male subjects in the fasted state is selected from: 0.6 to 1.4, 0.7 to 1.3, 0.8 to 1.2 and 0.9 to 1.1.

4. The unit dosage form of abiraterone acetate of claim 1, wherein:
   the [D50] of the abiraterone acetate is greater than 100 nm and less than one of: 1000 nm, 800 nm, 500 nm, 400 nm, and 300 nm; and
   the [D90] of the abiraterone acetate is greater than 300 nm and less than one of: 3000 nm, 2000 nm, 900 nm, 800 nm, and 700 nm.

5. The unit dosage form of abiraterone acetate of claim 1, wherein the [D4,3] of the abiraterone acetate is greater than 300 nm and less than one of: 1100 nm, 900 nm, and 800 nm.

6. The unit dosage form of abiraterone acetate of claim 1, wherein the dissolution rate of the abiraterone acetate in the unit dosage form is such that when the unit dosage form is tested in 900 ml of pH 4.5 phosphate buffer with 0.12% sodium lauryl sulfate using USP Apparatus II at 75 rpm, at least 70% of the abiraterone acetate dissolves in between 5 and 10 min.

7. The unit dosage form of abiraterone acetate of claim 1, wherein a 500 mg dose, upon oral administration to a population of healthy male subjects in the fasted state, provides a median blood plasma $t_{max}$ of 1 to 2.5 hrs.

8. The unit dosage form of abiraterone acetate of claim 1, wherein the 90% confidence interval of the mean blood plasma $C_{max}$ is a value between 50 and 120 ng/ml when a 500 mg dose is administered to healthy male subjects in the fasted state.

9. The unit dosage form of abiraterone acetate of claim 1, wherein the 90% confidence interval of the mean blood plasma AUC (0-∞) is a value between 240 and 650 h×ng/ml when a 500 mg dose is administered to healthy male subjects in the fasted state.

10. The unit dosage form of abiraterone acetate of claim 1, comprising abiraterone acetate at 5-50 wt. %, lactose monohydrate at 5-80 wt. %, sodium lauryl sulfate at 0.1-10 wt. %, microcrystalline cellulose at 5-80 wt. %, croscarmellose sodium at 1-15 wt. %, sodium stearyl fumarate at 0.01-10 wt. %, butylated hydroxyanisole at 0.001-1 wt. %, and butylated hydroxytoluene at 0.001-1 wt. %.

11. The unit dosage form of abiraterone acetate of claim 1, comprising abiraterone acetate at 10-30 wt. %, lactose monohydrate at 20-40 wt. %, sodium lauryl sulfate at 1-5 wt. %, microcrystalline cellulose at 20-60 wt. %, croscarmellose sodium at 2-10 wt. %, sodium stearyl fumarate at 0.1-2 wt. %, butylated hydroxyanisole at 0.01-2 wt. %, and butylated hydroxytoluene at 0.01-2 wt. %.

12. A unit dosage form of abiraterone acetate containing 125 mg of abiraterone acetate having a [D50] greater than 100 nm and less than 1200 nm, the unit dosage form further comprising lactose monohydrate, sodium lauryl sulfate, microcrystalline cellulose, croscarmellose sodium, sodium stearyl fumarate, butylated hydroxyanisole, and butylated hydroxytoluene;
   wherein the dissolution rate of the abiraterone acetate in the unit dosage form is such that when the unit dosage form is tested in 900 ml of pH 4.5 phosphate buffer with 0.12% sodium lauryl sulfate using USP Apparatus II at 75 rpm, at least 70% of the abiraterone acetate dissolves in between 5 and 15 minutes; and
   wherein a 500 mg dose, upon oral administration to a population of healthy male subjects in the fasted state, provides a mean blood plasma $C_{max}$ of 50-120 ng/ml and a mean blood plasma $AUC_{(0-\infty)}$ of 240-650 h×ng/ml.

13. The unit dosage form of abiraterone acetate of claim 12, wherein:
   the [D50] of the abiraterone acetate greater than 100 nm and is less than one of: 1000 nm, 800 nm, 500 nm, 400 nm, and 300 nm; and
   the [D90] of the abiraterone acetate is greater than 300 nm and less than one of: 3000 nm, 2000 nm, 900 nm, 800 nm, and 700 nm.

14. The unit dosage form of abiraterone acetate of claim 12, wherein the [D4,3] of the abiraterone acetate is greater than 300 nm and less than one of: 1100 nm, 900 nm, and 800 nm.

15. The unit dosage form of abiraterone acetate of claim 12, wherein the dissolution rate of the abiraterone acetate in the unit dosage form is such that when the unit dosage form is tested in 900 ml of pH 4.5 phosphate buffer with 0.12% sodium lauryl sulfate using USP Apparatus II at 75 rpm, at least 70% of the abiraterone acetate dissolves in between 5 and 10 min.

16. The unit dosage form of abiraterone acetate of claim 12, wherein a 500 mg dose, upon oral administration to a population of healthy male subjects in the fasted state, provides a median blood plasma $t_{max}$ of 1 to 2.5 hrs.

17. The unit dosage form of abiraterone acetate of claim 12, wherein the 90% confidence interval of the mean blood plasma $AUC_{(0-\infty)}$ is a value between 240 and 650 h×ng/ml when a 500 mg dose is administered to healthy male subjects in the fasted state.

18. The unit dosage form of abiraterone acetate of claim 12, wherein the 90% confidence interval of the mean blood plasma $C_{max}$ is a value between 50 and 120 ng/ml when a 500 mg dose is administered to healthy male subjects in the fasted state.

19. The unit dosage form of abiraterone acetate of claim 12, comprising abiraterone acetate at 5-50 wt. %, lactose monohydrate at 5-80 wt. %, sodium lauryl sulfate at 0.1-10 wt. %, microcrystalline cellulose at 5-80 wt. %, croscarmellose sodium at 1-15 wt. %, sodium stearyl fumarate at 0.01-10 wt. %, butylated hydroxyanisole at 0.001-1 wt. %, and butylated hydroxytoluene at 0.001-1 wt. %.

20. The unit dosage form of abiraterone acetate of claim 12, comprising abiraterone acetate at 10-30 wt. %, lactose monohydrate at 20-40 wt. %, sodium lauryl sulfate at 1-5 wt. %, microcrystalline cellulose at 20-60 wt. %, croscarmellose sodium at 2-10 wt. %, sodium stearyl fumarate at 0.1-2 wt. %, butylated hydroxyanisole at 0.01-2 wt. %, and butylated hydroxytoluene at 0.01-2 wt. %.

* * * * *